United States Patent [19]
Taylor et al.

[11] Patent Number: 5,425,713
[45] Date of Patent: Jun. 20, 1995

[54] SYSTEM AND METHOD FOR MONITORING, DISPLAYING AND RECORDING BALLOON CATHETER CONDITION INTERVAL AND INFLATION LOCATION DATA

[75] Inventors: Steven R. Taylor; Fred P. Lampropoulos, both of Salt Lake City, Utah

[73] Assignee: Merit Medical Systems, Inc., South Jordan, Utah

[21] Appl. No.: 223,470

[22] Filed: Apr. 4, 1994

Related U.S. Application Data

[63] Continuation-in-part of Ser. No. 853,522, Mar. 18, 1992, Pat. No. 5,300,027, which is a continuation of Ser. No. 324,938, Mar. 17, 1989, Pat. No. 5,135,488.

[51] Int. Cl.⁶ ..................... A61M 29/00; A61M 1/00
[52] U.S. Cl. .................... 604/100; 604/121; 604/49
[58] Field of Search .................... 604/96–103, 604/118, 121, 151–155, 49–54; 606/192–196; 600/18

[56] References Cited

U.S. PATENT DOCUMENTS

| | | |
|---|---|---|
| 383,940 | 6/1888 | Brinkerhoff . |
| 404,105 | 5/1889 | Overlach . |
| 446,125 | 2/1891 | Schirmer . |
| 577,682 | 2/1897 | Eissner . |
| 730,054 | 6/1903 | Sheets . |
| 1,661,818 | 3/1928 | Cook . |
| 1,707,880 | 4/1929 | Sheets . |
| 2,656,836 | 10/1953 | Hickey . |
| 2,672,866 | 3/1954 | Kater . |
| 2,699,168 | 1/1955 | Lewis . |
| 2,724,385 | 11/1955 | Lockhart . |
| 2,736,315 | 2/1956 | Feeney . |
| 2,764,978 | 10/1956 | Everett . |
| 3,080,866 | 3/1963 | Friedman . |
| 3,388,941 | 6/1968 | Marcus ..................... 294/4 |
| 3,478,937 | 11/1969 | Solowey ..................... 222/386 |
| 3,491,757 | 1/1970 | Arce . |
| 3,529,596 | 9/1970 | Garner . |
| 3,698,381 | 10/1972 | Federico et al. . |
| 3,720,199 | 3/1973 | Rishton et al. . |
| 3,884,229 | 5/1975 | Raines et al. . |
| 3,931,822 | 1/1976 | Marici . |

(List continued on next page.)

FOREIGN PATENT DOCUMENTS 545415 8/1957 Canada .
0119296 9/1984 European Pat. Off. .

(List continued on next page.)

OTHER PUBLICATIONS

Product catalog of Mansfield (1988).
Advertisement brochure of Mansfield entitled: "The Mansfield Trak Series." (1987).

(List continued on next page.)

Primary Examiner—John D. Yasko
Assistant Examiner—Adam J. Cermak
Attorney, Agent, or Firm—Workman Nydegger Seeley

[57] ABSTRACT

An electronically controlled syringe system for connection to a balloon catheter for automatically monitoring, displaying and recording inflation or deflation data. A syringe having a barrel and a plunger is used to apply or to release pressure to the balloon catheter or other balloon member. A transducer housed on the barrel of the syringe senses fluid pressures applied by the syringe. An electromagnetic signal output by the transducer means is input to a controller where the signal is digitally processed so as to derive and record therefrom electronic data representing the magnitude of applied fluid pressure and the length of time that positive fluid pressure is applied, which derived data is automatically displayed and recorded. The deflation of the balloon-type member is similarly processed and recorded. The controller is also programmable to permit input of various control parameters, such as a lesion location identifier, a maximum positive inflation pressure and maximum duration for applying pressure. Input of the various control parameters can be made at either of two redundant switch sets, where one of the switch sets is located on the syringe barrel.

20 Claims, 14 Drawing Sheets

U.S. PATENT DOCUMENTS

| | | | |
|---|---|---|---|
| 3,966,358 | 6/1976 | Heimes et al. | 417/12 |
| 3,985,123 | 10/1976 | Herzlinger et al. | |
| 3,992,926 | 11/1976 | Berryhill | 73/80 |
| 4,016,871 | 4/1977 | Schiff | |
| 4,057,050 | 11/1977 | Sarstedt | |
| 4,063,662 | 12/1977 | Drummond et al. | 222/31 |
| 4,086,653 | 4/1978 | Gernes | 364/564 |
| 4,106,002 | 8/1978 | Hogue, Jr. | 340/626 |
| 4,182,344 | 1/1980 | Benson | 128/207.15 |
| 4,254,773 | 3/1981 | Waldbillig | 128/348 |
| 4,261,360 | 4/1981 | Perez | |
| 4,266,550 | 5/1981 | Bruner | 128/349 |
| 4,267,846 | 5/1981 | Kontos | 128/765 |
| 4,285,340 | 8/1981 | Gezari et al. | 128/205.24 |
| 4,323,071 | 4/1982 | Simpson et al. | 128/343 |
| 4,332,254 | 6/1982 | Lundquist | 128/344 |
| 4,370,982 | 2/1983 | Reilly | 604/98 |
| 4,384,470 | 5/1983 | Fiore | 73/4 R |
| 4,404,974 | 9/1983 | Titus | 128/670 |
| 4,418,392 | 11/1983 | Hata | 364/571 |
| 4,439,185 | 3/1984 | Lundquist | 604/97 |
| 4,444,335 | 4/1984 | Wood et al. | 222/43 |
| 4,446,715 | 5/1984 | Bailey | 73/1 R |
| 4,446,867 | 5/1984 | Leveen et al. | |
| 4,460,355 | 7/1984 | Layman | 604/118 |
| 4,466,426 | 8/1984 | Blackman | |
| 4,504,268 | 3/1985 | Herlitze | |
| 4,522,194 | 6/1985 | Normann | |
| 4,526,196 | 7/1985 | Pistillo | 137/557 |
| 4,546,760 | 10/1985 | Suzuki et al. | |
| 4,557,269 | 12/1985 | Reynolds et al. | 128/675 |
| 4,568,335 | 2/1986 | Updike et al. | 604/211 |
| 4,573,978 | 3/1986 | Reilly | 604/240 |
| 4,583,917 | 4/1986 | Shah | 417/63 |
| 4,583,974 | 4/1986 | Kokernak | 604/211 |
| 4,585,010 | 4/1986 | Ascer et al. | 128/673 |
| 4,596,255 | 6/1986 | Snell et al. | 128/697 |
| 4,597,381 | 7/1986 | Oumi et al. | 128/6 |
| 4,600,015 | 7/1986 | Evans et al. | 128/780 |
| 4,601,701 | 7/1986 | Mueller, Jr. | 604/83 |
| 4,610,256 | 9/1986 | Wallace | 128/675 |
| 4,621,646 | 11/1986 | Bryant | 128/692 |
| 4,651,783 | 3/1987 | Demer et al. | 128/344 |
| 4,658,829 | 4/1987 | Wallace | 128/672 |
| 4,662,355 | 5/1987 | Pieronne et al. | 128/1 |
| 4,672,974 | 6/1987 | Lee | 128/673 |
| 4,710,179 | 12/1987 | Haber et al. | 604/211 |
| 4,715,854 | 12/1987 | Vaillancourt | 604/191 |
| 4,723,938 | 2/1988 | Goodin et al. | 604/99 |
| 4,743,230 | 5/1988 | Nordquest | 604/97 |
| 4,756,706 | 7/1988 | Kerns et al. | 604/66 |
| 4,758,223 | 7/1988 | Rydell | 604/90 |
| 4,781,192 | 11/1988 | Demer | 128/344 |
| 4,787,368 | 11/1988 | Kageyama | 600/18 |
| 4,787,429 | 11/1988 | Valentini et al. | 141/383 |
| 4,796,606 | 1/1989 | Mushika | 600/18 |
| 4,799,491 | 1/1989 | Eckerle | 128/672 |
| 4,817,629 | 4/1989 | Davis et al. | 128/748 |
| 4,819,637 | 4/1989 | Dormandy | 128/325 |
| 4,820,271 | 4/1989 | Deutsch | 604/99 |
| 4,825,876 | 5/1989 | Beard | 128/675 |
| 4,830,013 | 5/1989 | Maxwell | 128/637 |
| 4,832,692 | 5/1989 | Box et al. | 604/99 |
| 4,838,864 | 6/1989 | Peterson | 604/100 |
| 4,858,615 | 8/1989 | Meinema | 128/668 |
| 4,865,581 | 9/1989 | Lundquist et al. | 600/18 |
| 4,872,483 | 10/1989 | Shah | 137/557 |
| 4,877,035 | 10/1989 | Bogen et al. | 128/673 |
| 4,896,671 | 1/1990 | Cunningham et al. | 128/642 |
| 4,901,731 | 2/1990 | Miller | 128/675 |
| 4,906,244 | 3/1990 | Pinchuk | 606/194 |
| 4,907,596 | 3/1990 | Schmid et al. | 128/672 |
| 4,919,121 | 4/1990 | Rydell et al. | 604/97 |
| 4,940,459 | 7/1990 | Noce | 604/97 |
| 4,974,774 | 12/1990 | Nakagawa et al. | 600/18 |
| 5,004,472 | 4/1991 | Wallace | 606/194 |
| 5,009,662 | 4/1991 | Wallace | 606/192 |
| 5,011,468 | 4/1991 | Lundquist et al. | 600/18 |
| 5,019,041 | 5/1991 | Robinson | 604/97 |
| 5,021,046 | 6/1991 | Wallace | 606/97 |
| 5,024,668 | 6/1991 | Peters et al. | 606/194 |
| 5,059,167 | 10/1991 | Lundquist et al. | 600/17 |
| 5,084,060 | 1/1992 | Freund et al. | 606/192 |
| 5,086,777 | 2/1992 | Hishii | 128/675 |
| 5,135,488 | 8/1992 | Foote et al. | 604/97 |
| 5,215,523 | 6/1993 | Williams et al. | 604/97 |
| 5,242,408 | 9/1993 | Jhuboo et al. | 604/152 |
| 5,259,838 | 11/1993 | Taylor et al. | 604/97 |
| 5,279,563 | 1/1994 | Brucker et al. | 604/98 |
| 5,300,027 | 4/1994 | Foote et al. | 604/100 |
| 5,383,855 | 1/1995 | Nicholson et al. | 604/100 |
| 5,387,194 | 2/1995 | Williams et al. | 604/97 |

FOREIGN PATENT DOCUMENTS

| | | |
|---|---|---|
| 0230966A3 | 1/1985 | European Pat. Off. |
| 0149866 | 7/1985 | European Pat. Off. |
| 0396353 | 11/1990 | European Pat. Off. |
| 1242737 | 8/1960 | France |
| 2083364 | 3/1982 | United Kingdom |
| WO81/02664 | 10/1981 | WIPO |
| WO92/17721 | 10/1992 | WIPO |

OTHER PUBLICATIONS

Advertisement brochure of Mansfield entitled: "The Mansfield Series 3000 Intra-Aortic Balloon Pump". (1988).

(List continued on next page.)

OTHER PUBLICATIONS

Advertisement brochure of Medex, Inc. for Medflator inflation system. (1991).

Advertisement brochure of Mansfield for Digiflator inflation syringe with an attached digital pressure gauge. (undated).

Mansfield instruction brochure for the Digiflator. (1991).

Advertisement brochure of Condor Medical for Trasflator Infrared System. (undated).

Advertisement brochure of VasTek for the Inter/Com Inflation System Computer. (undated).

Brochure of VasTek disclosing Inter/Com and inflation syringe entitled: "Reach Out and Touch the Future". (undated).

"ACS Accessories Offer Optimum Efficiency in Your Angioplasty Procedures," Eli Lilly and Company (undated).

Advertising brochure or North America Instrument Corporation entitled "The NAMIC 10 cc Angiographic Syringe Features."(Jul. 1988).

Advertising brochure of Spectramed, Inc.; produce prochure for "CONTROLEASE Disposable Control Syringe"; and product brochure for control syringe of COEUR Laboratories, Inc. (undated).

"Clearing the Path for a Healthy Heart," *Tristate: The Cincinnati Enquirier Magazine*, Oct. 23, 1988.

"Coronary Angioplasty," Krames Communications, 1985.

"Good News for People with Only Two Hands," SciMed Life Systems, Inc. (undated).

"Health—Critics of Angioplasty Worry About Inflated Success Claims," *U.S. News & World Report*, Jul. 25, 1988, p. 65.

"Inflation PRO: A New Dual-Support System for Angioplasty," Baxter Healthcare Corporation (undated).

"PTCA Safe and Efficacious Performed Together With Diagnostic Angiography in Selected Cases," *Cardiovascular News*, May 1988, p. 8.

"USCI Wizard Disposable Inflation Device," C. R. Bard, Inc. (1987).

SYSTEM AND METHOD FOR MONITORING, DISPLAYING AND RECORDING BALLOON CATHETER CONDITION INTERVAL AND INFLATION LOCATION DATA

This is a continuation-in-part of application Ser. No. 07/853,522, filed Mar. 18, 1992, now U.S. Pat. No. 5,300,027, which is a continuation of application Ser. No. 07/324,938, filed Mar. 17, 1989, now U.S. Pat. No. 5,135,488.

A portion of the disclosure of this patent document contains material to which a claim of copyright protection is made. The copyright owner has no objection to the reproduction by anyone of the patent document or the patent disclosure 2 as it appears in the Patent and Trademark Office patent file or records, but reserves all other rights with respect to the copyrighted work.

Appendix A, referred to herein, may be found in the microfiche appendix contained in the Patent and Trademark Office file for this patent document. The microfiche appendix is comprised of one microfiche having sixty-one frames.

BACKGROUND OF THE INVENTION

1. Field of the Invention

This invention relates to syringe systems that are used for controlling the inflation and deflation conditions of a balloon-tipped catheter, and more particularly to a system and method which utilize an electronically monitored syringe system to assist in the control of balloon catheter inflation and deflation pressures and to automatically record balloon catheter condition interval data.

2. The Present State of the Art

Balloon-tipped catheter systems have been known and used in the medical arts for a number of years in connection with a variety of different kinds of procedures which are used, for example, in various fields of medicine, such as urology, gynecology, cardiology and others. Particularly in connection with the treatment of coronary artery disease, the use of balloon-tipped catheters and their associated syringe systems have become widely used.

Coronary artery disease is the narrowing of the arteries that feed oxygen-rich blood to the heart. The coronary arteries are located on the top of the heart and return oxygenated blood to the heart. Since the heart is a muscle whose primary job is to pump oxygenated blood throughout the body, the heart needs adequate amounts of oxygen to properly function. Thus, when the coronary arteries become narrowed or blocked (a condition known as "stenosis"), angina can result. Angina is a symptom of coronary artery disease characterized by chest pain or pressure that can radiate to the arm or jaw, and is caused by a lack of oxygen-rich blood to the heart muscle. Coronary artery disease with its accompanying symptom of angina results from atherosclerosis, which is a build up of waxy material called plaque inside the arteries. When this happens, under exertion or stress, the heart demands more oxygen but the narrowed coronary arteries cannot supply enough oxygen-rich blood to meet the demand, resulting in angina.

Up until about ten years ago, there were two basic methods of treating coronary artery blockages: with medicine or by performing coronary artery bypass surgery. Various kinds of medication could be administered which would decrease the work of the heart by slowing the heart rate, dilating the blood vessels, or lowering blood pressure. However, such medicinal treatment did not cure coronary artery blockage, which thus remained and which would therefore continue to present a risk that at some point the blockage would become serious enough to require surgical intervention.

In coronary artery bypass surgery, a blood vessel from the chest or leg is grafted beyond the point of blockage so that the blood detours past the blockage in order to reach the heart. In some severe cases, multiple bypasses are performed. As is well known, coronary artery bypass surgery is expensive, is a high risk procedure, and often requires prolonged hospitalization and recovery periods.

About ten years ago, another method for treating coronary artery disease was developed, called balloon coronary angioplasty or, more technically, percutaneous transluminal coronary angioplasty (PTCA). PTCA is a much less traumatic procedure than coronary artery bypass surgery. PTCA takes about two hours and can be done under local anesthesia, with the result that often a patient can be back on his feet and active in a matter of days. Because PTCA is much less expensive and less traumatic than bypass surgery and yet in many cases still effectively removes blockage, PTCA has experienced a dramatic increase in the number of such procedures performed each year. For example, according to some reports, as recently as 1987 some 200,000 patients suffering from coronary artery disease were treated by PTCA. Since coronary artery disease remains the number one cause of death, with (as of 1987) some six million reported cases in the U.S. alone, PTCA may be expected to continue to play an important role in the treatment of coronary artery disease.

In performing PTCA, an introducer sheath is inserted through an incision made in an artery of an arm or the groin. An x-ray opaque dye is injected into the coronary artery through a catheter that is introduced through the sheath. The dye enables the doctor, through the use of real time x-ray techniques, to clearly view the arteries on a television monitor and to thereby locate the artery blockage. A balloon-tipped catheter with a guide wire at the end of it is then advanced through the artery to the point of the blockage with the help of the x-ray monitor.

As schematically illustrated in FIGS. 1A–1C, a balloon catheter 10 is advanced to the middle of a blockage 12. Catheter 10, which is filled with a fluid and is coupled at its other end to a control syringe, is manipulated by a cardiologist. Once balloon catheter 10 is in place, utilizing the control syringe, balloon 10 is inflated for 20 to 60 seconds as shown in FIG. 1B. Balloon catheter 10 is then deflated and this procedure is repeated typically several times to compress the plaque on the arterial wall, as shown in FIG. 1C. After the results are checked, the balloon catheter and guide wire are then removed.

As will be appreciated, notwithstanding that PTCA is a much less traumatic procedure than coronary artery bypass surgery, nonetheless exacting control with respect to inflation pressure and duration of the inflation periods is essential to the safety of the patient. For example, when the balloon catheter is completely inflated so as to begin compressing the plaque, blood flow to the heart is thereby temporarily shut off. This creates the potential for initiating cardiac arrest. Accordingly, the pressure exerted on the artery by the balloon catheter as well as the duration of the blockage created by inflating the balloon catheter must both be carefully controlled by the attending cardiologist and other personnel. The inflation pressures, the duration of each inflation, and the time between each inflation must be based on the cardiologist's assessment of the health of the patient and the patient's ability to withstand such a temporary stoppage of blood flow to the heart.

In the past, PTCA syringe systems have utilized syringe systems which are equipped with standard pressure gauges that are utilized to sense and read the pressure used for purposes of inflating a balloon catheter. Human observation of stop clocks and the like have been used to control the duration of the inflation.

While these prior art techniques have been widely used with success, there is still a serious risk of human error when using such systems. The gauges used on such syringe systems are often awkward and difficult to accurately read, and are also subject to malfunction. Thus, improper recording of inflation pressure and/or duration may occur. Accordingly, there is a need for the cardiologist and/or clinician to be able to improve the degree of control and precision with respect to the inflation procedure. There is also a need to be able to accurately record the procedure data so that in the event of any later question with respect to whether the procedure was properly carried out, there is an accurate record from which to answer such questions. The system and method of the present invention provide an effective solution to these problems which has not heretofore been fully appreciated or solved.

SUMMARY OF THE INVENTION

The system and method of the present invention have been developed in response to the present state of the art and, in particular, in response to the problems and needs in the art not heretofore fully or completely solved by syringe inflation systems used in connection with PTCA procedures. However, it is not intended that the system and method of the present invention will necessarily be limited solely to PTCA procedures since they will also find useful application with potentially many kinds of procedures which require the utilization of inflatable balloon members for various kinds of medical procedures. Thus, it is an overall object of the present invention to provide a system and method which provide for more accurate measurement, monitoring and recording of the balloon inflation and deflation condition and the respective durations thereof, as well as the pressures used for inflation of a balloon-type member in connection with any such inflation of a balloon-type member, catheter or otherwise.

Another important object of the present invention is to provide a system and method whereby state of the art electronic technology can be utilized to assist the cardiologist or clinician in accurately measuring, monitoring and recording durations of time that the balloon member is in a condition of inflation or deflation, and the highest inflation pressure which he or she achieved when utilizing a syringe system to inflate a balloon catheter, and which will at the same time automatically electronically record and store the balloon catheter condition and the duration of the condition so as to permit the data pertaining to the procedure to be later printed out and thus accurately documented and saved for later reference.

Another important object of the present invention is to provide an improved syringe system and method of electronic monitoring and recording which increases the convenience and safe utilization of a balloon catheter or other balloon-type inflation member.

These and other objects and features of the present invention will become more fully apparent from the following more detailed description taken in conjunction with the drawings and claims, or may be learned by the practice of the invention.

Briefly summarized, the foregoing and other objects are achieved in an electronically monitored syringe system that is connected to a balloon catheter or other inflatable balloon-type device through tubing. The syringe comprises a barrel and a plunger selectively operable to increase fluid pressure applied to the balloon catheter through the connecting tubing by sliding the plunger further into the barrel, and to then remove the applied pressure by returning the plunger to the rear of the barrel. A transducer means for sensing fluid pressure applied by the syringe is placed in fluid communication with the syringe and the connecting tubing. The transducer means thereby senses applied fluid pressure and outputs an electromagnetic signal proportional to the sensed pressure. The electromagnetic signal output by the transducer means is then electronically processed so as to derive and record therefrom electronic data representing the status of pressure applied to the balloon catheter.

A magnitude of positive pressure would generally indicate an inflation balloon condition and pressure below such magnitude would indicate a deflation balloon condition. Also derived and recorded is the length of time from the end of one balloon inflation condition to the start of the next balloon inflation condition. The numerical value of the highest positive inflation pressure applied to the balloon member is recorded during a balloon condition of inflation. The electronic data representing the balloon condition of inflation or deflation and the respective duration of each such condition is then automatically displayed and/or recorded.

The system also comprises a display means for selectively outputting a visual display of the magnitude of the applied pressure and the corresponding length of time that inflation pressure is applied to the balloon catheter or other balloon-type member with respect to each inflation thereof as well as displaying the balloon condition when the balloon is not inflated (e.g. deflation) and the corresponding duration of time elapsed from the end of the prior balloon inflation condition.

The electronic control system used in conjunction with the system and method of the present invention may also be optionally designed to permit the system user to select and input various control parameters. One such control parameter that the operator may input is the locations of various artery blockages, also called lesions, that are intended operative sites. Other control parameters that optionally may be selected and input by the system user include the selection of how and where input is to be accepted from the user in the present system. Other control parameters that may be selected and input are options such as a maximum positive inflation pressure that is to be applied, a maximum duration for applying positive inflation pressure, initializing the date and time of the procedure, and retrieving and displaying balloon condition data previously recorded for any prior inflation or deflation of the balloon catheter.

The system includes a means for a system user to select and input various control parameters. The input means is preferrably situated as an integral part of the syringe so as to be located inside the sterile field in which medical personnel operate.

The balloon condition and related data that is derived and accumulated may be printed out on a printer both textually and by graphical representation. In this manner, the system and method of the present invention provide not only more convenient operation of the syringe when inflating the balloon catheter or other balloon-type member, but also a much safer and more accurate procedure which can be used to effectively alert a cardiologist or clinician when the appropriate levels and status of pressure, absence thereof, and respective durations thereof have been reached with respect to any particular balloon condition. The system is efficient and easy to operate while at the same time providing improved convenience and overall safety, and also providing accurate documentation of balloon condition data for later reference.

BRIEF DESCRIPTION OF THE DRAWINGS

The presently preferred embodiments and the presently understood best mode of the invention will be described with additional detail through use of the accompanying drawings, wherein corresponding parts are designated by the same reference numerals throughout, and in which.

DETAILED DESCRIPTION OF THE PREFERRED EMBODIMENTS

The following detailed description is divided into two parts. In part I, the overall system is described including a description of the syringe system, the transducer means and electronic controller by reference to FIGS. 1 through 5. Part II describes the method by which the system of the present invention is used to electronically monitor, display and automatically record balloon condition data, including a detailed description of one presently preferred method for programming the digital processor used in the electronic controller by reference to FIGS. 6A-6I.

I. THE SYSTEM

A. General Environment and Intended Utility of the System

Figure 1A:
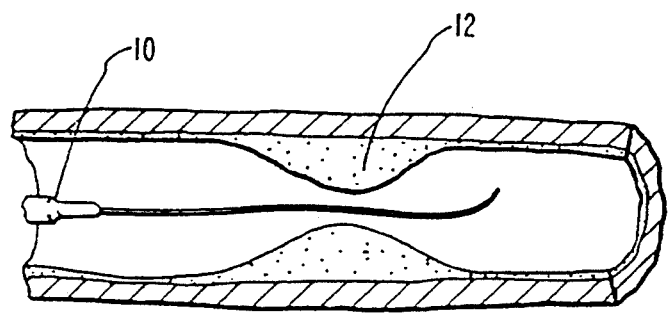
FIGS. 1A-1C are partial cross-sectional views which schematically illustrate a conventional balloon catheter being placed within a vessel such as a coronary artery containing a blockage, and showing the manner in which the blockage is essentially compressed by inflation of the balloon catheter.
Figure 1B:
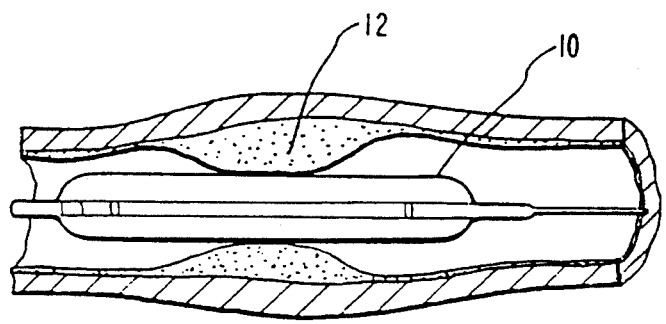
Figure 1C:
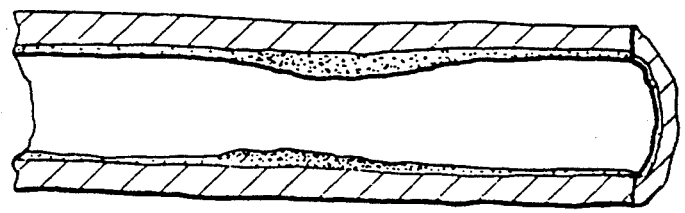

As noted above, the system and method of the present invention have been developed in response to specific needs which have been found to exist in connection with techniques that are currently in use according to the present state of the art which has developed in connection with PTCA procedures. As described in connection with FIGS. 1A-1C, PTCA is a surgical procedure used for treating coronary artery disease wherein balloon catheter 10 is inserted through an incision made in the artery of an arm or a leg and is then advanced through the artery by means of a guide catheter and assisted by means of an x-ray opaque dye. Balloon catheter 10 is advanced until it is located at the middle of blockage 12. Once located at the middle of blockage 12, balloon catheter 10 is then inflated (see FIG. 1B) to a pressure that is typically between 7 and 10 atmospheres for a duration of between 20 to 60 seconds. Balloon catheter 10 is then deflated and the procedure is repeated a number of times, slightly increasing the inflation pressure each time so as to further compress and thereby reduce blockage 12 created by the buildup of plaque along the wall of the artery. Once this series of inflations and deflations is completed and the artery is cleared, as shown in FIG. 1C, balloon catheter 10 is removed.

While the system and method of the present invention are particularly useful in connection with the aforementioned PTCA procedure, the system and method of the invention are not intended to be necessarily limited to use in connection with PTCA. Rather, it is contemplated that the system and method of the invention will find useful application with respect to any procedure requiring the use of an inflatable balloon-type member. Moreover, while in PTCA the inflation pressure which is applied to balloon catheter 10 is applied hydraulically by means of the syringe and connecting tubing which are all filled with a sterile liquid such as a solution of saline and contrast medium, in some potential applications it may be necessary or desirable to apply the inflation pressure pneumatically. Accordingly, as used herein, the term "fluid pressure" is intended to apply either to a hydraulically or a pneumatically applied inflation pressure.

The term balloon, or balloon catheter, is intended herein to mean a balloon-type member, including a balloon catheter, which is inflated by a syringe and equivalents thereof.

B. The Presently Preferred Syringe System and Electronic Controller: FIGS. 2-5

1. System Components, Generally

The system of the present invention is comprised of a syringe that is connected to a balloon catheter or other balloon-type member through tubing. The syringe is used to apply fluid pressure to the balloon catheter through the tubing so as to inflate the balloon catheter after it has been deflated for a selected duration, and to deflate the balloon catheter after it has been inflated for a selected duration. The system is also comprised of a transducer means for sensing applied fluid pressure and for outputting an electromagnetic signal proportional to the sensed fluid pressure. The transducer means function may be performed by a variety of devices. The transducer means may be a piezoresistive semiconductor transducer, a fiber optic substrate emitting light at frequencies or colors that are proportional to the pressures being applied to the substrate, or a radio transmitter in electrical communication with a pressure sensitive substrate for which changes in modulated frequencies are proportional to the pressures being applied to the substrate. The electromagnetic signal output from the transducer means is reflected back, transmitted, or otherwise communicated to a conversion means for converting the electromagnetic signal to an electrical digital signal that is proportional to the electromagnetic signal output by the transducer means.

The transducer means is preferably in fluid communication with the syringe and the tubing connected to the balloon catheter. The system additionally comprises the aforesaid conversion means which is in communication with the transducer means and which serves to convert the electromagnetic signal output by the transducer means to an electrical digital signal. A digital processor means, which is connected to the conversion means, receives the electrical digital pressure signal that is output by the conversion means and processes the electrical signal so as to derive and record therefrom electronic data representing inflation pressure applied to the balloon catheter as well as the length of time the inflation pressure is applied to the balloon catheter each time it is inflated. The system also similarly derives and records from the electrical digital pressure signal electronic data representing a balloon deflation condition and the time elapsed since the end of the previous balloon inflation condition.

The system is also further comprised of display means, which is electrically connected to the digital processor means, for selectively outputting a visual display of the inflation pressure and the corresponding length of time the inflation pressure is applied to the balloon catheter during each inflation, as well as visually displaying a notice that the balloon is in a deflated condition and the corresponding duration of the deflated condition. An input means is included in the system enabling the system user to interactively respond to displayed system prompts so that the system user may accept options offered by the system as well as acknowledge and correct problems detected by the system.

2. System Components; Detailed Description of Drawings

Figure 2:
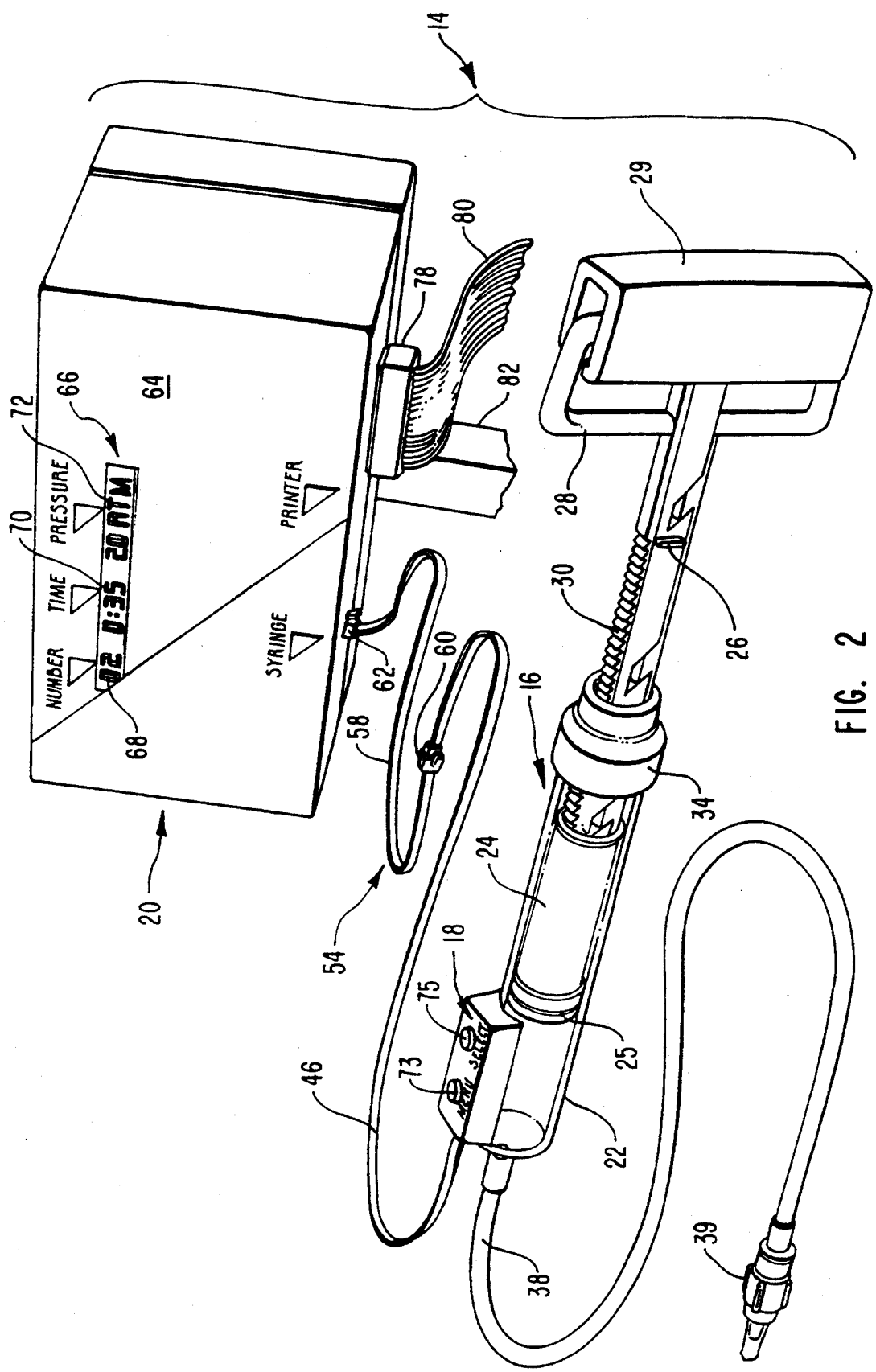
FIG. 2 is a perspective illustration showing the system of the present invention and, in particular, illustrating a syringe with tubing for connection to a balloon catheter, and a transducer means mounted on the syringe and electrically connected to an electronic controller.
Figure 3:
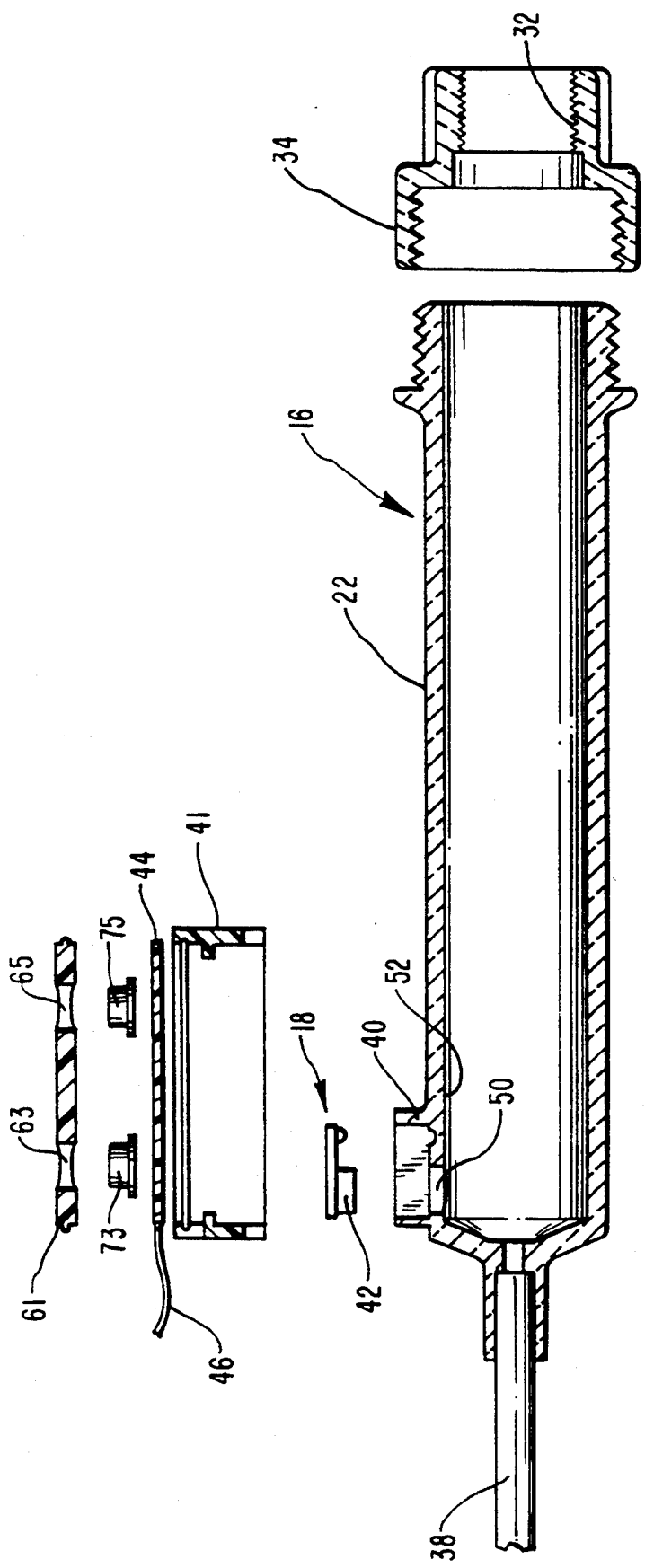
FIG. 3 is a partial cross-sectional view of the syringe barrel that more particularly illustrates one presently preferred structure for placing the transducer means in fluid communication with the interior of the syringe and the tubing which is connected to the balloon catheter.

In the preferred embodiment illustrated in FIG. 2, the overall system is generally designated at 14. A controller 20 contains the data processing and visual display circuitry required for pressure monitoring. A syringe is generally designated at 16. With reference to FIGS. 2 and 3 taken together, syringe 16 is comprised of a barrel 22 typically molded from transparent plastic material to permit inspection of the contents thereof. A syringe plunger 24 (FIG. 2) is slidably mounted within barrel 22 and is secured therein of means by a cap 34 which can be threadingly or otherwise securely attached at the end of barrel 22. Syringe plunger 24 has a threaded portion 30 which mates with corresponding threads 32 (see FIG. 3) of cap 34.

The proximal end of plunger 24 is provided with a soft rubber bulb 25 which engages the interior of barrel 22 in a fluid-tight fit such that by sliding syringe plunger 24 further into barrel 22, positive pressure exerted on the fluid contained within syringe 16 and the connecting tubing 38 will be applied to balloon catheter 10 (See FIG. 1) which is connected to tubing 38 by means of a rotatable luer connector 39. Similarly, by withdrawing syringe plunger 24 shown in FIG. 2 toward the rear of barrel 22, the positive pressure will be released that was exerted in balloon catheter 10 shown in FIG. 1.

Rapid movement of syringe plunger 24 is accommodated by means of a trigger mechanism comprising a spring-activated trigger 28 which can be retracted into handle 29 so as to disengage threaded portion 30 from corresponding threads 32 of cap 34. This permits plunger 24 to freely slide in either direction within syringe barrel 22. By releasing the compression on trigger 28 relative to handle 29, threaded portion 30 is then permitted to engage corresponding threads 32 of cap 34 so that thereafter syringe plunger 24 can only be advanced or retracted by screwing plunger 24 either clockwise or counterclockwise, respectively. Thus, rapid application or release of pressure applied to balloon catheter 10 can be accomplished by compressing trigger 28 against handle 29 followed by movement of syringe plunger 24 to the position desired for the approximate pressure to be applied. This can then be followed by releasing trigger 28 and rotating plunger 24 within syringe barrel 22, which will permit a slow, gradual adjustment of syringe plunger 24 to effect the pressure that is desired.

It will be appreciated that insofar as providing for application and release of positive inflation pressure, this function of syringe 16 of the system could be provided by any of a number of syringe systems which are conventional or known in the art. However, the syringe illustrated and generally described in connection with FIGS. 2 and 3 is presently preferred in connection with the system and illustrates the presently contemplated best mode of the syringe 16. A description of the general features of syringe 16 is contained in U.S. Pat. No. 5,057,078 which is incorporated herein by reference.

An example of the transducer means of the system of the present invention is generally designated in FIG. 3 as transducer assembly 18. The body of syringe barrel 22 has a small rectangular syringe housing 40 formed at the leading end of barrel 22 as an integral part thereof. Syringe housing 40 communicates through a small circular opening 50 formed in the sidewall of syringe barrel 22 with the interior thereof for the purpose of providing fluid communication from the interior of barrel 22 and connecting tubing 38 to transducer assembly 18, as hereinafter more fully described.

As used herein, the term "fluid communication" is intended to mean the pneumatic or hydraulic transmission (direct or indirect) of fluid pressures exerted within syringe barrel 22 and connecting tubing 38 to balloon catheter 10 so that such fluid pressures can be sensed by transducer assembly 18. Direct transmission of such fluid pressures would occur, for example, when a diaphragm of a piezoresistive semiconductor transducer is placed into contact (either pneumatically or hydraulically, or a combination of both) with a fluid contained in a closed system, as would be the case in the preferred embodiment illustrated and described herein. Indirect transmission could be said to occur, for example, where the transducer means is coupled to a diaphragm that in turn contacts the fluid contained in a closed system.

Figure 5A:
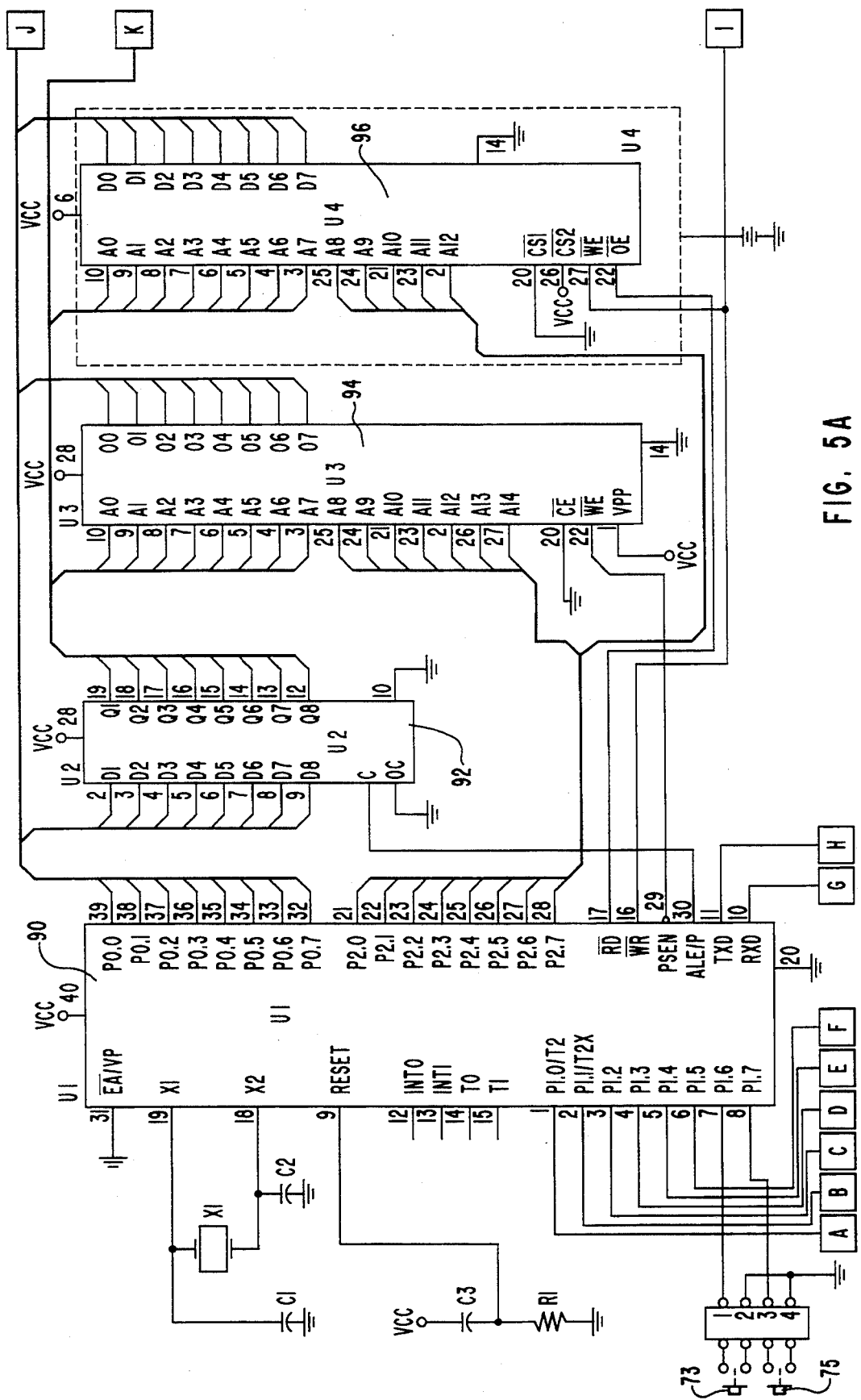
FIGS. 5A through 5D taken together constitute a detailed electrical schematic diagram which illustrate, as an example, the presently preferred embodiment and presently understood best mode for implementing the electronics of the system and method of the present invention.
Figure 5B:
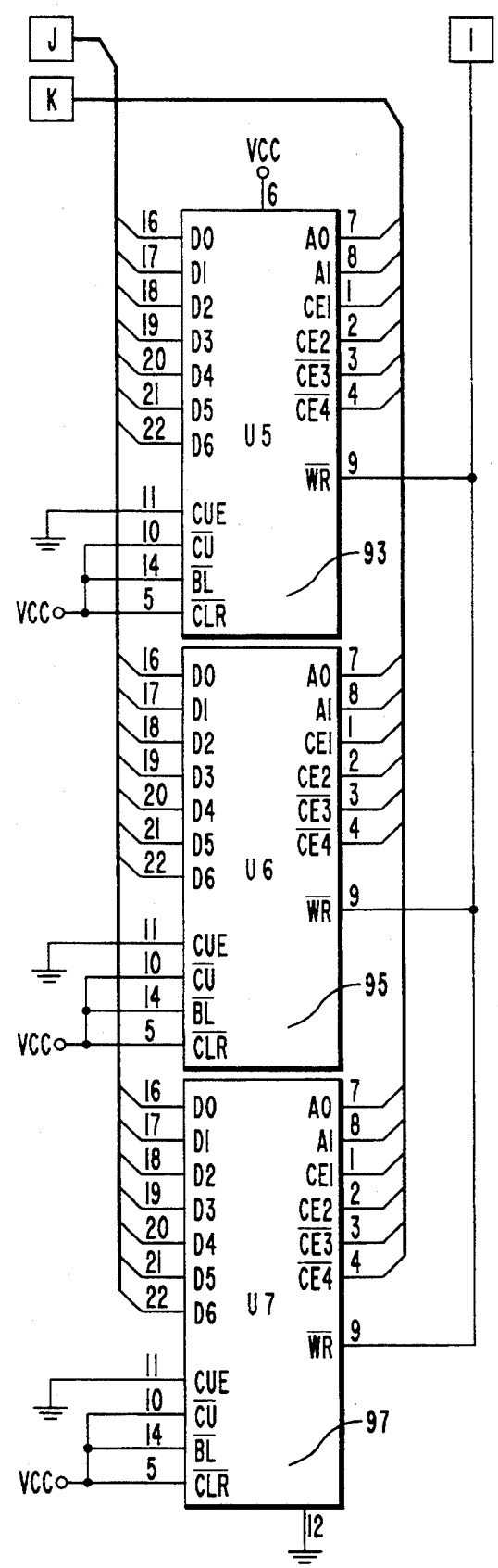
Figure 5C:
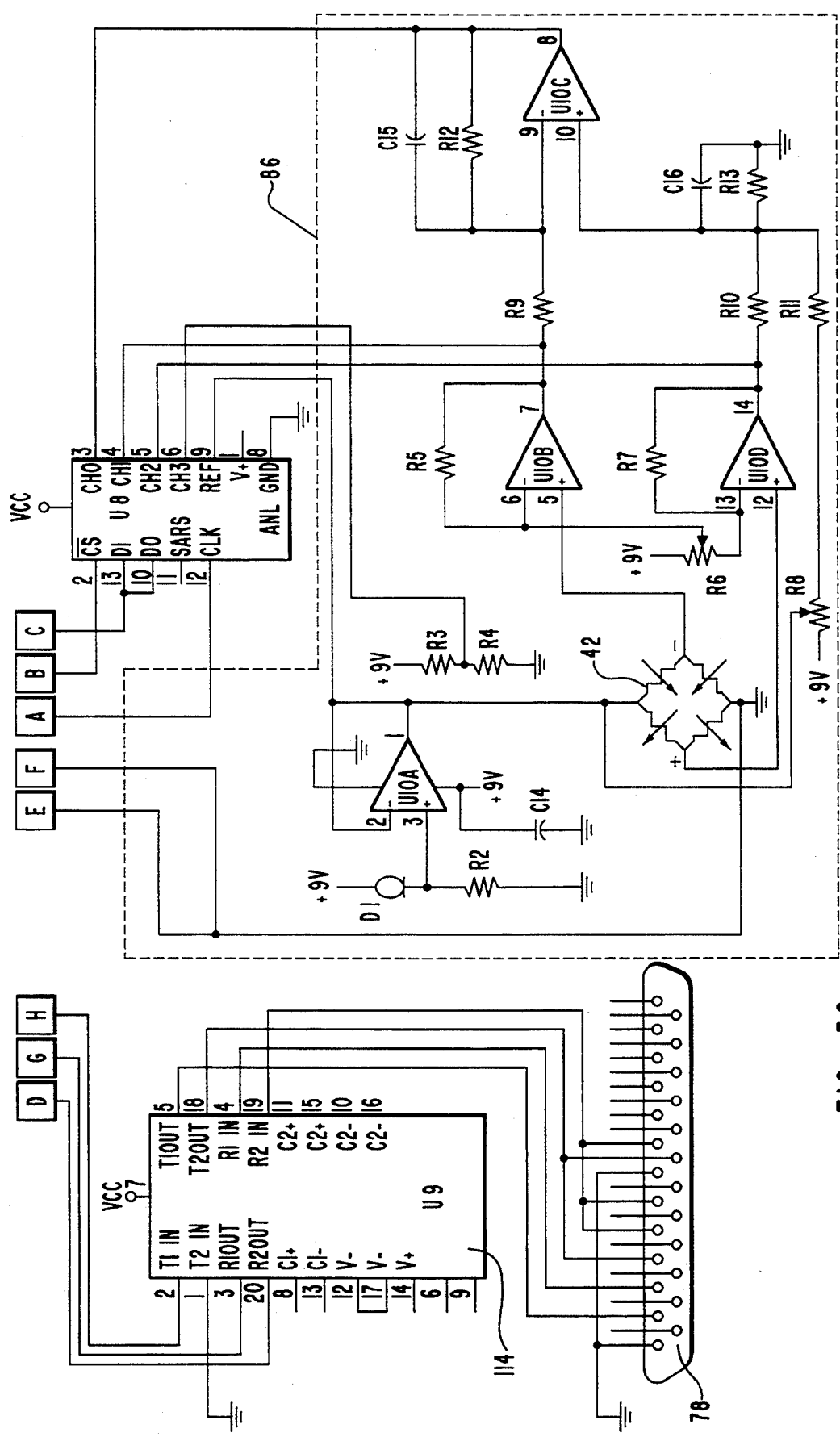

In FIG. 3, transducer assembly 18 preferably incorporates a transducer 42 that is a piezoresistive semiconductor integrated circuit which provides a Wheatstone bridge, as shown in the detailed electrical schematic at FIG. 5C at the corresponding reference numeral to be further described herein.

Transducer 42 is seated within syringe housing 40 upon which is placed lower housing 41, the same of which may be bonded to syringe barrel 22. Transducer 42 has interconnects to a printed circuit board or small ceramic substrate 44 which contains additional circuitry for providing temperature compensation and calibration of transducer 42, and to which is connected an electrical cable 46. Ceramic substrate 44 further contains circuitry interconnected for receiving input from a select switch 73 and a menu switch 75, both of syringe 16. The ceramic substrate 44 is seated on lower housing 41, as are select switch 73 and menu switch 75.

Upper housing 61, having a first and a second button well 63, 65 respectively, is sealingly seated upon lower housing 41 over switches 73, 75, respectively. Button wells 63, 65 are preferably integrally sealed with switches 73, 75 to prevent leakage of the highly conductive fluid within the syringe barrel 22 via circular opening 50. Additionally, switches 73, 75 are preferably constructed of elastomeric materials so as to further guard against leakage of conductive fluids in syringe 16. The end of electrical cable 46 is assembled with ceramic substrate 44 and piezoresistive semiconductor transducer 42, as illustrated in FIG. 3, and placed within syringe housing 40, and then secured by a suitable potting compound and permanently enclosed by means of upper housing 61 placed on top of lower housing 41 over syringe housing 40. In this manner, the entire transducer assembly 18 is formed as an integral attachment to syringe barrel 22.

Circular opening 50 may be filled, for example, with a silicone gel which will permit transmission of the fluid pressures exerted by means of syringe 16 through circular opening 50 so that such pressures can be sensed by transducer 42, while at the same time isolating integrated circuit board 44 and transducer 42 from coming into contact with electrical currents or fluid contained in syringe barrel 22.

Stops 26 (see FIG. 2) are formed on syringe plunger 24 so as to prevent bulb 25 of syringe plunger 24 from being inserted to the point where it would otherwise close off circular opening 50.

While in the preferred embodiment the transducer means has been illustrated and described as a piezoresistive semiconductor transducer 42 which is integrally mounted to syringe barrel 22, it should be appreciated that the preferred embodiment is illustrative only and is not to be construed as limiting the scope of the invention. For example, the semiconductor transducer could be located at the end of connecting tubing 38 attached through a T-connector to tubing 38 and could therefore be located at a position remote from syringe 16, as for example on an I.V. stand or mounted as part of the electronic circuitry contained inside of controller 20. As previously stated, the transducer means could also comprise transducer types other than the piezoresistive semiconductor type illustrated and described in the preferred embodiment. As additional examples, the conventional strain gauge transducer which has been known and used in the art for many kinds of different pressure monitoring applications, or the fiber optic pressure transducer using electromagnetic energy could also be used.

With further reference to FIG. 2, an electrical cable generally designated at 54 is comprised of a first length 46 and a second length 58. First length 46 of cable 54 is permanently attached at one end to transducer assembly 18 in the manner described above in connection with FIG. 3. The other end of first length 46 terminates in a conventional connector 60 which attaches to second length 58 of cable 54. Second length 58 of cable 54 in turn attaches by a conventional connector 62 to the electronic circuitry contained in controller 20. Advantageously, by providing a point at connector 60 which is intermediate transducer assembly 18 and controller 20, transducer assembly 18 and syringe 16 can be disconnected from controller 20 so that syringe 16 can be conveniently moved to a different location for testing or the like while still maintaining the sterility of syringe 16 and transducer assembly 18. It is intended that controller 20 be outside of the sterile field so that it may not necessarily be sterile, while sterility of first length 46 of cable 54, transducer assembly 18, and syringe 16 can be maintained at all times in that they are intended to be within the sterile field.

With continued reference to FIG. 2, the electronic circuit means and display means of the system of the present invention are illustrated in the preferred embodiment as comprising part of controller 20. The specific electronic circuitry which is used for purposes of processing the electrical signals output by transducer assembly 18 through cable 54 is contained inside of controller 20 and is more particularly illustrated in FIGS. 4 and 5A-5D, as hereinafter more fully described. The display means of the system is shown by way of example of the same in the illustrated embodiment as comprising, in addition to corresponding parts of the electronic circuitry, a digital readout as generally designated at 66 which is part of the control panel 64.

Menu switch 73 of syringe 16 in conjunction with programmable aspects of the system, when activated by pressing menu switch 73, will cause a series of optionally selectable functions to be displayed at digital readout 66. Select switch 75 of syringe 16 can then be used to input various control parameters as well as causing controller 20 to retrieve and display previously recorded data, as hereinafter more fully described. Controller 20 is also equipped with a conventional connector 78 for a printer cable 80 in communication with a printer (not shown) so that data which is recorded in a memory component of controller 20 can also be selectively printed out for permanent documentation and later reference.

A function contemplated herein enables the system user to select a visually displayed menu option to print out several blank entry lines on the printer attached via cable 80 to the system after an inflation. This function is provided so that notes can be manually written on the printout from the printer on the blank entry lines. Such notes would typically comprise comments as to any aspect of the particular inflation and would serve to document a clinician's handwritten history of an inflation event. The memory component of controller 20 is updated to store the event that a note line was requested by the system user.

The system of the present invention has the capability of printing a graphical representation of inflation pressure versus time on a printer that is connected to the system, via cable 80, during the one or more inflations for which a graphically represented printout is desired. The system's baud rate is contemplated to be sufficient to communicate to a peripheral printer so as to facilitate real time printing of graphics.

Digital readout 66 of control panel 64 is shown in the illustrated embodiment of FIG. 2 as comprising a conventional LED or LCD alphanumeric display having twelve or any other suitable number of controllable display positions for outputting numbers or letters. Digital readout 66 is preferably also divided into a number display portion 68 which displays the number of each discrete condition of the balloon catheter, respectively, inflation conditions or deflation conditions. A time display portion 70 is used to display the current date and time, as well as to display user input control data with respect to a maximum duration for applied positive pressure, as desired, and is also used to display the duration of the respective balloon conditions of inflation or deflation, and to display a signal to a system user if a selected time of duration has been reached. A pressure portion 72 displays user input selected control data with respect to a maximum positive inflation pressure desired in connection with any inflation, selection of the pressure units (e.g., atmospheres or pounds per square inch), and is also used to display the current inflation pressure, zero pressure, or a status notice of negative pressure in syringe barrel 22, and to signal the system when a selected maximum inflation pressure has been reached.

Controller 20 can be conveniently located on a stand 82 at a point which is easily visible by the cardiologist or clinician using system 14 and can be conventionally powered on or off. Controller 20 is also plugged into a conventional AC wall outlet from which the power is derived for purposes of running controller 20, and is also provided with a battery-backed memory which provides an internal clock and timer and which retains data and time-keeping functions after controller 20 is powered off.

In the presently preferred embodiment, the electrical circuitry comprises means for amplifying the electromagnetic signal output by the transducer means; means for converting the amplified signal from an analog to a digital form; digital processor means for processing the digital form of the signal so as to derive therefrom digital data from which the status of pressure applied to the balloon catheter during a condition of inflation and the corresponding duration thereof and during of a condition of deflation and the corresponding duration thereof, the magnitude of the applied pressure, and whether the applied pressure corresponds to a first or a subsequent inflation or deflation of the balloon catheter which may be output in the numerical sequence thereof; data memory means for storing the digital data derived by the digital processor; and program memory means for storing machine-readable instructions utilized by the digital processor means to derive, store, retrieve and display digital data and to optionally display a series of functions for selection at the display means of various control parameters.

Figure 4:
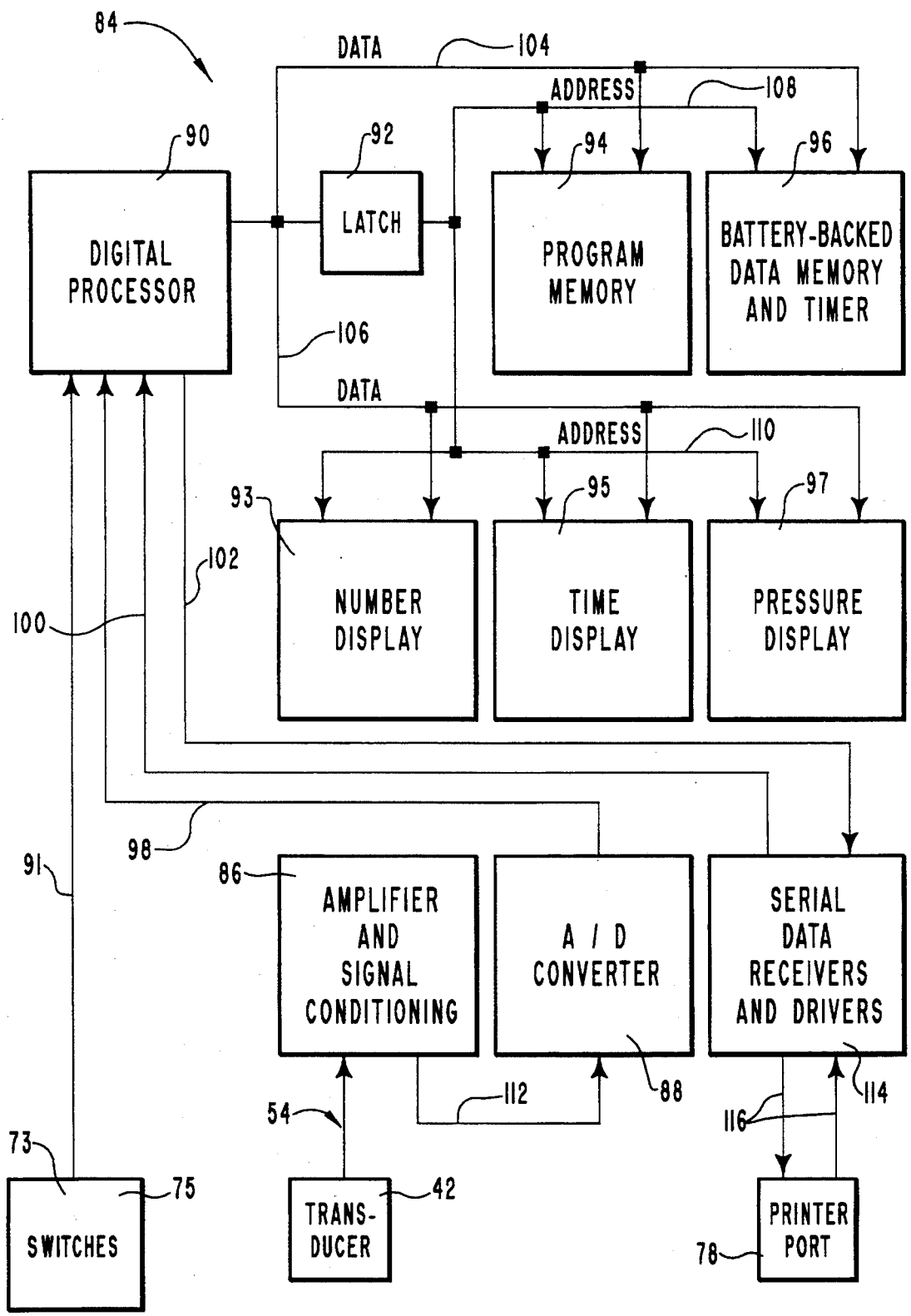
FIG. 4 is a functional block diagram which schematically illustrates the primary components of one presently preferred electronic circuit used in connection with the electronic controller.

It should be appreciated that the particular circuit components and circuit design which are illustrated in FIGS. 5A through 5D are intended merely as an example of the presently preferred embodiment and the presently understood best mode of implementing the overall functions which are represented by the block diagram of FIG. 4. FIGS. 5A through 5D illustrate in detail the electrical schematic diagrams showing the pin numbers and interconnections for each of the integrated circuit components and the other circuit elements used in the implementation of the preferred embodiment. Of course other circuit designs can be devised that would also work satisfactorily using either software driven digital processing circuitry or hardware based circuit design.

With particular reference to the presently preferred embodiment of the circuitry as generally designated at 84 in FIG. 4, transducer 42 is electrically connected by means of cable 54 to an analog circuit 86 which provides amplification and signal conditioning and serves as an example of the amplifying means. As more particularly illustrated in FIG. 5C by the portion of the circuit enclosed by the dashed box 86, amplifier and signal conditioning circuit 86 is shown in the preferred embodiment as a 100 millivolt full scale differential amplifier with an adjustable differential gain of forty to one, which is provided by amplifiers U10B, U10D, and U10C. In a preferred embodiment, the conversion means signal conditioning circuitry would be within these amplifiers, from which the aforementioned monitor offset is derived.

From circuit 86 the amplified signal is then input as schematically represented at line 112 in FIG. 4, and as illustrated at terminal CH0 of an integrated circuit U8 in FIG. 5C, to a conventional analog to digital (A/D) converter circuit 88. A/D converter 88 serves to illustrate the means for converting the amplified signal from an analog to a digital form by outputting a series of corresponding digital signals which identify the analog signal sensed and input by the transducer means. As shown in reference to FIG. 5C, in the presently preferred embodiment, A/D converter 88 is comprised of an integrated circuit U8. The particular integrated circuit U8 used in the implementation of the circuitry, as well as the identification of each of the parts used in the detailed electrical schematic of FIGS. 5A through 5D, is set forth in Table I at the end of the detailed description.

With continued reference to FIGS. 4 and 5A through 5D, the digitized signal is output by A/D converter 88, as schematically represented by line 98 and as illustrated in greater detail in FIG. 5A, to a digital processor 90. Digital processor 90 serves as an example of the digital processor means, and is illustrated in FIG. 5A as integrated circuit U1. Digital processor 90 is controlled by machine-readable instructions stored in a program memory 94 which are communicated as schematically illustrated in FIG. 4 by means of a data bus 104 running between digital processor 90 and program memory 94. Program memory 94 serves as an example of the program memory means. The particular program instructions carried out by digital processor 90 are more particularly illustrated and described in reference to the flow charts of FIGS. 6A-6I, as hereinafter more fully described in the Method description of part II. Program instructions are addressed by digital processor 90 through latch circuit 92 and an address bus schematically represented at line 108 (FIG. 4). Switches 73, 75 situated on syringe barrel 22 act as input keys to digital processor 90, as shown in FIG. 4 by leader line 91.

Digital processor 90 in FIG. 5A has leads E and F connecting to pins 5 and 6, respectively. As shown in FIG. 5C, leads E and F are routed to transducer 42 through two switches, each lead having its own switch. The interconnection between digital process 90, pins 5 and 6, and transducer 42 via switchable leads E and F is to coordinate and facilitate the operation of menu button 73 and select button 75 on syringe barrel 22.

Briefly summarized, the instructions stored in program memory 94 are utilized by digital processor 90 to derive from the digitized data the fluid pressure conditions applied by syringe 16 to balloon catheter 10 in FIG. 1 and to display the sensed pressure conditions at pressure display portion 72 of control panel 64 (see FIG. 2). The applied fluid pressure conditions are also automatically recorded by digital processor 90 and stored in a data memory 96, the latter of which serves as an example of the data memory means. The output of the digital data to pressure display portion 72 is transmitted by way of a bus 106 schematically shown in FIG. 4 and the corresponding electronic circuitry 97 (FIGS. 4 and 5B) which is used to drive pressure display portion 72. Digital processor 90 can also be programmed to display positive inflation pressure which is output at pressure display portion 72 in units of either atmospheres or pounds per square inch as selected by the system user by means of using menu switch 73 and select switch 75 as hereinafter more fully explained. Further, pressure display portion 72 can also display a deflation condition notice, such as the characters "NEG," when the pressure is less than zero, and will also output a zero (0) when the applied pressure is not less than zero but is below a predetermined numerical value representing a balloon condition of inflation.

Digital processor 90 can also be utilized according to the programmed instructions contained in program memory 94 to monitor and thus assist in the control of the maximum positive inflation pressure to be applied to the balloon catheter by a system user inputting for display at pressure display portion 72 a maximum positive pressure using menu and select switches 73, 75. The maximum positive pressure parameter is sent from the corresponding display circuitry 97 on bus 106 and bus 104 to data memory 96. Thereafter, once the user input maximum positive pressure parameter is reached in the balloon catheter, digital processor 90 will cause the pressure display portion 72 to flash to signal the system user that the maximum positive pressure has been reached. This advantageously assists the system user in more carefully controlling the procedure used with respect to each inflation event of balloon catheter 10.

A selected duration for which positive inflation pressure is to be applied to balloon catheter 10 can also be input and displayed at time display portion 70 using menu switch 73 and select switch 75. The corresponding display circuitry 95 thus sends the selected duration time through data buses 106 and 104 to data memory 96. Accordingly, the programmed instructions contained in program memory 94 will thereafter cause digital processor 90 to begin counting the duration once positive inflation pressure begins to be applied. The count will be output by digital processor 90 at time display portion 70, and will flash once the selected duration has been reached to signal the system user that positive inflation pressure has been applied for the desired length of time. This duration monitor feature significantly enhances the ability of the system to carefully assist the system user in controlling the inflation procedure according to the selected parameters.

Data memory 96 is battery-backed so as to retain all data stored therein even when controller 20 is switched off, and so as to provide an internal timer for the date and time data and for clocking any selected maximum duration times input as described above. The system contemplated herein stores a history of at least 256 inflations and deflation events in data memory 96. The system disclosed herein could also be provided with a wrap around memory to prevent loss of newly acquired data. For balloon catheter operations, a system memory of 256 events is foreseeably sufficient for most purposes. By wrap-around memory, it is meant that once the 256th event has been recorded in the system memory, the system will record the 257th event by over writing the first event of the 256 events. This over writing or wrap-around aspect is transparent to the system user in that no error message, such as "FULL MEMORY" is displayed for the system user, as none is necessary. This method of storing event data is also known as "FIFO" or "First-In-First-Out" in that the oldest data is the first data to be over written with the new data once the data memory is full.

Each of the maximum pressure and time control parameters which are displayed at pressure display portion 72 and time display portion 70 are stored as noted above in data memory 96. In this manner, these appropriate control parameters are utilized by the program stored in program memory 94 and are also automatically recorded in data memory 96 for later reference. In a similar manner, once a pressure is applied to balloon catheter 10 that is in an inflation or deflation condition, digital processor 90 will automatically time the corresponding duration of the balloon condition and this information will likewise be recorded and stored in data memory 96 for later reference, along with a numerical identification displayed at number display portion 68 which identifies whether the particular inflation event is the first time the balloon catheter has been inflated or whether the inflation or deflation is a respective subsequent inflation or deflation.

Each time balloon catheter 10 is inflated it is discretely identified by number, and the maximum inflation pressure and time duration data corresponding to that inflation event are not only displayed but are also automatically recorded and stored in data memory 96. Accordingly, each time an inflated balloon is deflated it is discretely identified by number and the duration of elapsed time since the end of the prior balloon inflation condition and the deflation status of the balloon condition are not only displayed but are also automatically recorded and stored in data memory 96.

Latch circuit 92 is used to control the gating of address data from digital processor 90 to the respective program and data memories 94 and 96 and display circuits 93, 95 and 97 as is conventional in the art. In the detailed schematic of FIG. 5A, latch circuit 92 is illustrated at integrated circuit U2, while the program memory 94 and data memory 96 are shown as the integrated circuits U3 and U4, the particular specifications of which are identified in Table I. Integrated circuits for the number, time and pressure display circuits 93, 95 and 97 are also shown in FIG. 5B at integrated circuits U5, U6 and U7 with their corresponding identifications in Table I.

In addition to digital readout 66, system 14 also provides for output of the recorded data from digital processor 90 through serial data lines 100, 102 to a serial data receiver and driver circuit 114, which in turn is connected as schematically illustrated at lines 116 to a printer port 78 to which printer cable 80 is connected. The serial data receivers and drivers are shown as a conventional integrated circuit identified at U9 in FIG. 5C, and which is an RS232 driver and serial transmitter.

Figure 5D:
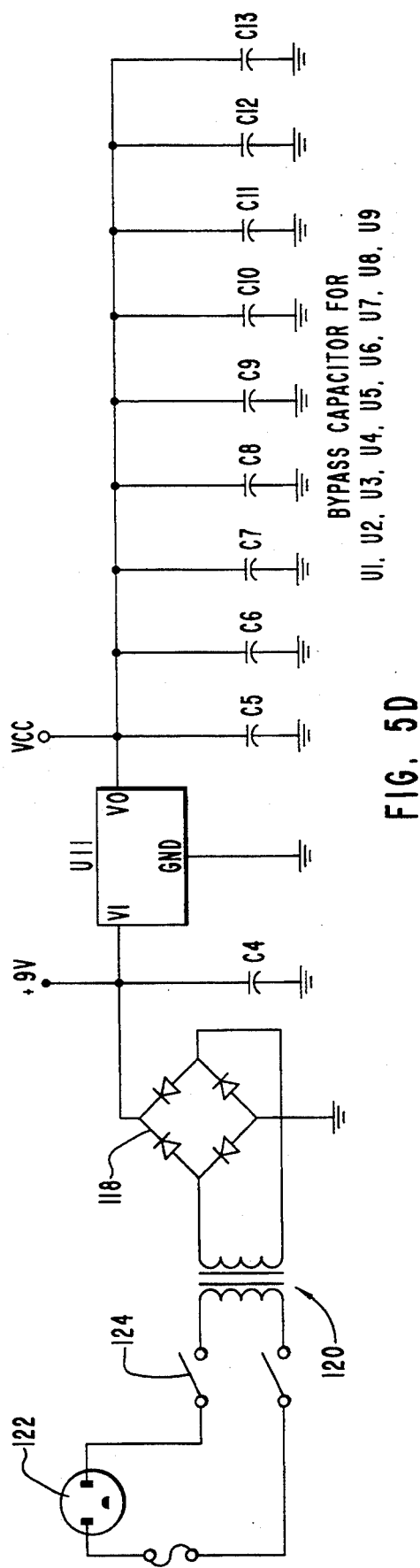

The supply voltage used for driving the integrated circuits and other active circuit elements shown in the detailed schematic diagram of FIGS. 5A through 5D is supplied by means of a transformer 120 in FIG. 5D which is connected at its output to a full wave bridge rectifier 118. The output of rectifier 118 is regulated by integrated circuit U11 which is a voltage regulator. The capacitors C5–C13 serve as noise suppression filters for each of the integrated circuits U1 through U9. With further reference to FIG. 5D, the switch 124 represents the switch on the back of controller 20 which is used to turn controller 20 on and off and which connects controller 20 through a conventional cord and socket plug 122 to an AC outlet.

II. THE METHOD

Attention is next turned to a detailed description of the presently preferred method by which the system of the present invention is used to monitor, display and automatically record balloon catheter condition data. Particular reference is now made to FIGS. 6A–6H which illustrate one presently preferred embodiment of the instructions which may be utilized to control the digital processor means. As will be appreciated by those of ordinary skill in the art, and as noted above, while the system and method as described in reference to the preferred embodiments herein illustrate the system and method as implemented using state of the art digital processing design and corresponding program instructions for controlling the processor, the system and method could also be implemented and carried out using a hardware design which accomplishes the necessary electronic processing, which is thus intended to be embraced within the scope of various of the claims as set forth hereinafter.

Figure 6A:
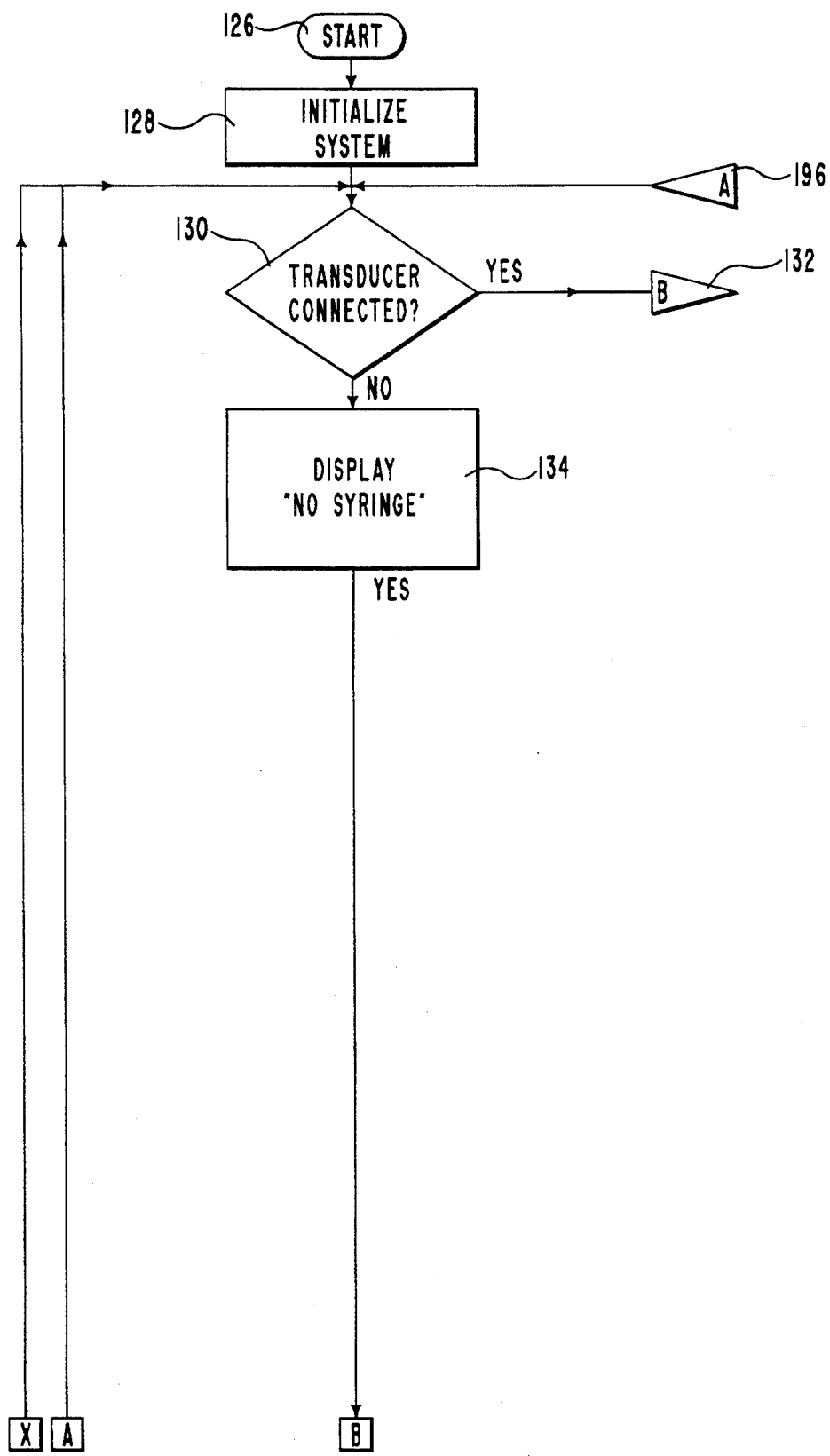
FIGS. 6A through 6F taken together illustrate a flow chart showing one presently preferred method for programming the digital processor in accordance with the method of the present invention.

With reference to FIG. 6A, when controller 20 is powered the program starts as indicated at step 126 and then immediately moves to step 128 which causes the program to initialize. At step 128, the appropriate program instructions are loaded into digital processor 90. The program then moves to step 130 where it checks to determine whether transducer 42 has been electrically connected by cable 54 to the electronic circuitry housed in controller 20. If transducer 42 is connected, the program then moves as indicated at B-flag 132 to the portion of the programmed instructions illustrated in FIG. 6F. If transducer 42 has not yet been electrically connected to controller 20, the program causes a message to be output on digital readout 66 signifying that transducer 42 is disconnected (e.g. "NO SYRINGE") at step 134.

Menu and selection switches 73, 75 of syringe 16 can be employed by the system user to answer program prompts that are displayed on digital readout 66 as "yes" or "no" responses to the prompts. When so prompted by the prompt program, the system user presses menu switch 73 to answer "yes" and select switch 75 to answer "no".

Figure 6B:
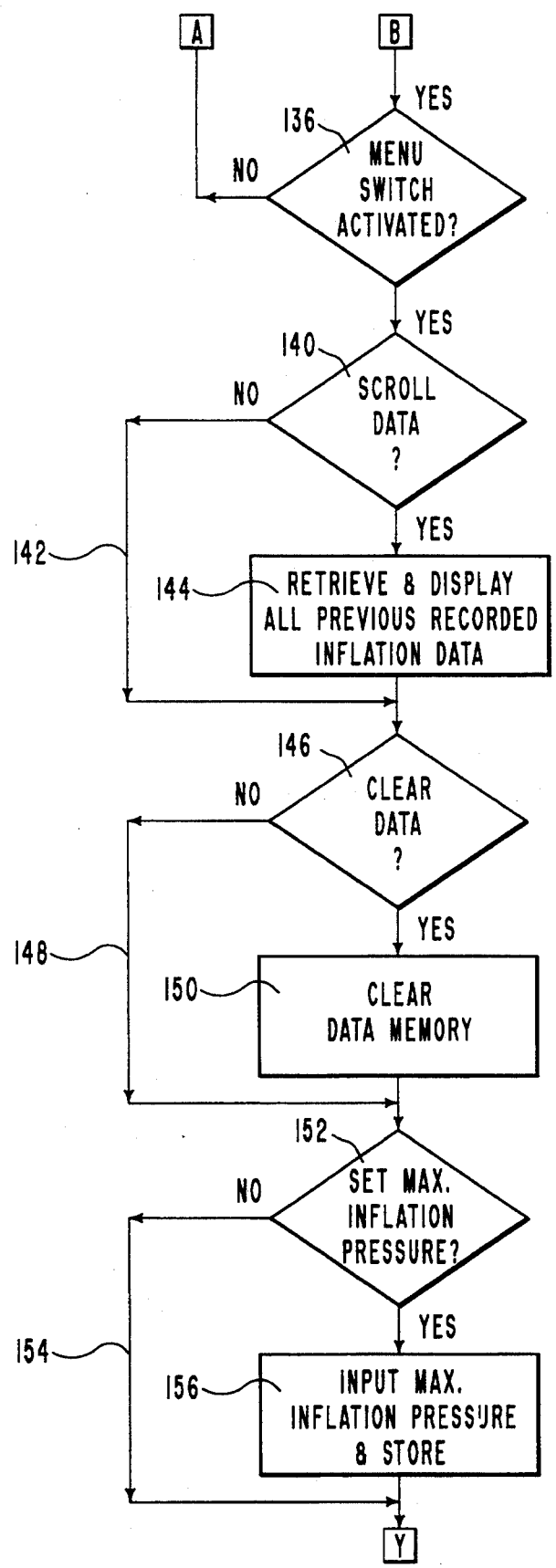

After step 134, the program moves to step 136 of FIG. 6B, to check whether menu switch 73 has been activated and if not, the program returns to step 130 of FIG. 6A and continues in the loop of steps 130, 134, and 136 until menu switch 73 is activated, after prompting the system user at step 136 in FIG. 6B to press menu switch 73.

Once menu switch 73 is activated at step 136 in FIG. 6B, then the program proceeds to step 140 in FIG. 6B and causes the digital readout 66 to display a message inquiring whether the balloon catheter condition data previously recorded by the program is to be scrolled in an output format visually displayed at digital readout 66. If the system user desires to review the previously recorded balloon condition data by the scroll function, select switch 75 is activated and the program then implements step 144 of FIG. 6B which causes previously recorded balloon condition for each balloon condition occurrence to be retrieved in sequence and displayed.

Scrolled data is displayed at digital readout 66. In the case of an inflation balloon catheter condition, the highest inflation pressure applied during the inflation condition and the duration of the inflation condition corresponding to each inflation number is retrieved and displayed. In the case of a deflation balloon catheter condition, a deflation condition notice and the duration corresponding to each deflation number is retrieved and displayed. The inflation condition data and the deflation condition data displayed during the scroll function will appear in the order that they respectively occurred.

If at step 140 in FIG. 6B the system user does not wish to scroll the previously recorded balloon condition data, menu switch 73 is again activated which causes the program to skip step 144 as schematically illustrated at line 142 so as to proceed with the next inquiry as represented at step 146 in FIG. 6B.

At step 146 in FIG. 6B the program causes a message to be displayed on digital readout 66 inquiring whether previously recorded balloon condition data which has been stored in data memory 96 is to be cleared. If select switch 75 is activated, this causes digital processor 90 to clear the previously recorded balloon condition data from data memory 96, as indicated at step 150 in FIG. 6B. If the previously recorded balloon condition data is not to be cleared from data memory 96, as indicated by the operator depressing menu switch 73 the program skips past step 150 as illustrated at line 148 in FIG. 6B and moves to the next inquiry as represented at step 152.

At step 152 in FIG. 6B the program causes digital readout 66 to display an inquiry with respect to whether an upper limit is to be set with respect to the maximum positive inflation pressure to be applied with respect to the next inflation event. If so, select switch 75 will be activated and is used to input the selected maximum positive inflation pressure through data transfer buses 106 and 104 (see FIG. 4), to data memory 96 for later reference. If the option to set a maximum inflation pressure is not selected at step 152, menu switch 73 is activated which causes the program to skip step 156 as illustrated at line 154 in FIG. 6B and move to the next inquiry as represented at box "Y" and step 158 in FIG. 6C.

Figure 6C:
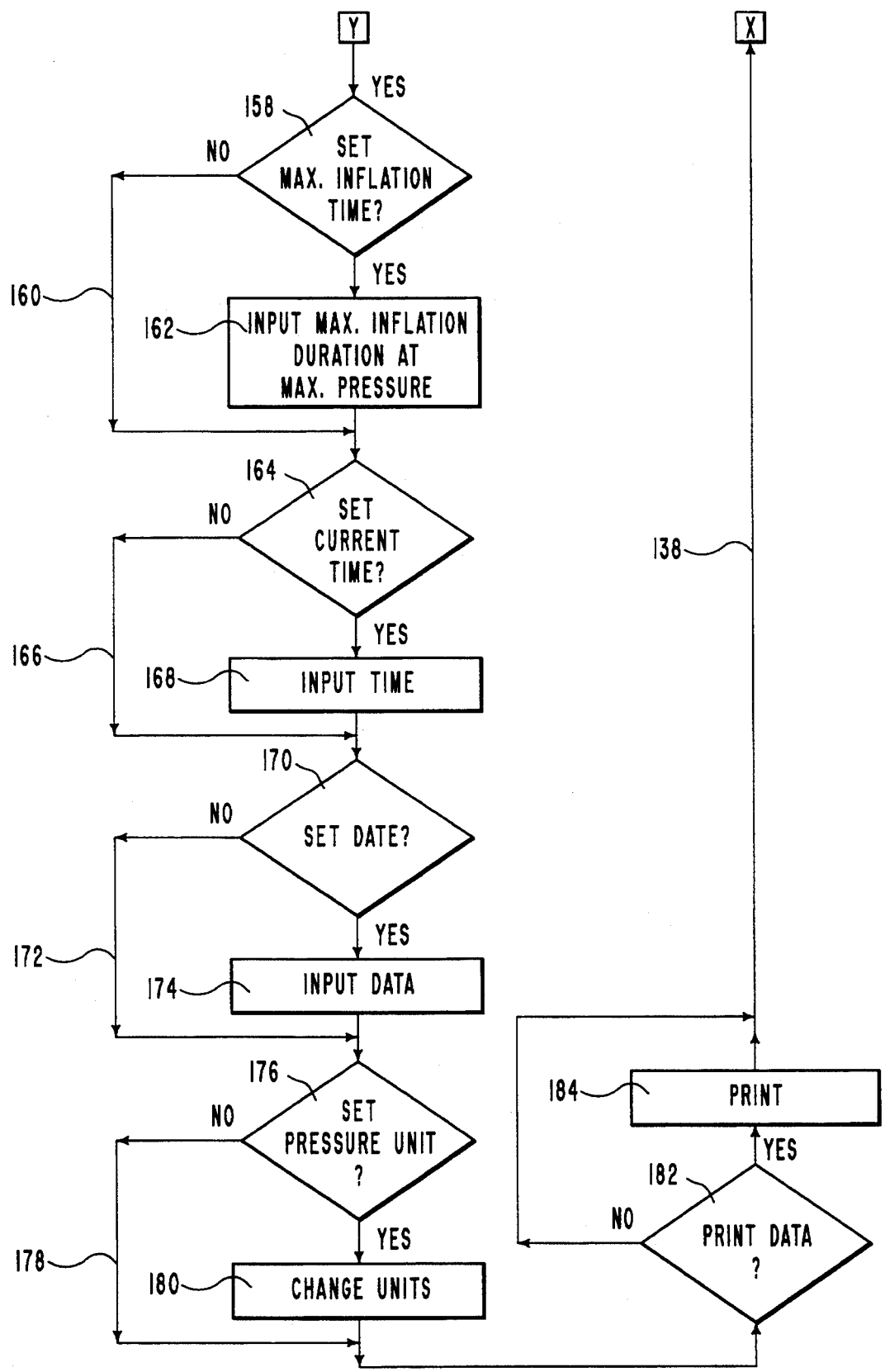

At step 158 in FIG. 6C the program displays a message at digital readout 66 inquiring whether the maximum duration for application of positive pressure is to be selected. If so, select switch 75 is again activated which causes the program to move to step 162 and select switch 75 is then used to input for display at the time display 70 the selected duration. This selected duration is input through data transfer buses 106 and 104 to data memory 96 for later reference.

In a manner similar to that described above in connection with the preceding prompt and response steps, the program continues to inquire whether the current time and date are to be set, as represented in FIG. 6C at steps 164 and 170, respectively, and if so, by utilizing select switch 75 as described above, current date and time may be entered for display at time display 70. However, the internal clock that is part of the integrated circuit U4 (see FIG. 5A) will typically make it unnecessary to enter these parameters. The program then moves through the series of steps represented at 176, 180, 182, and 184 where it determines the pressure units to be displayed at pressure display portion 72 as well as determining whether balloon condition data is to be printed. After the print inquiry has been responded to by utilization of the appropriate menu or select switches 73, 75 the program returns as illustrated at line 138 in FIG. 6C to step 130 in FIG. 6A.

As will be appreciated from the foregoing, the portion of the program which is carried out according to the flow chart of FIGS. 6A through 6C pertains to that part of the program which permits a series of optionally selectable functions to be sequentially displayed for purposes of inputting various control parameters which are later utilized in displaying and automatically recording the balloon condition data, as well as utilizing these control parameters to alert the system user when selected limits are reached with respect to maximum positive inflation pressure and duration of positive inflation pressure.

Figure 6D:
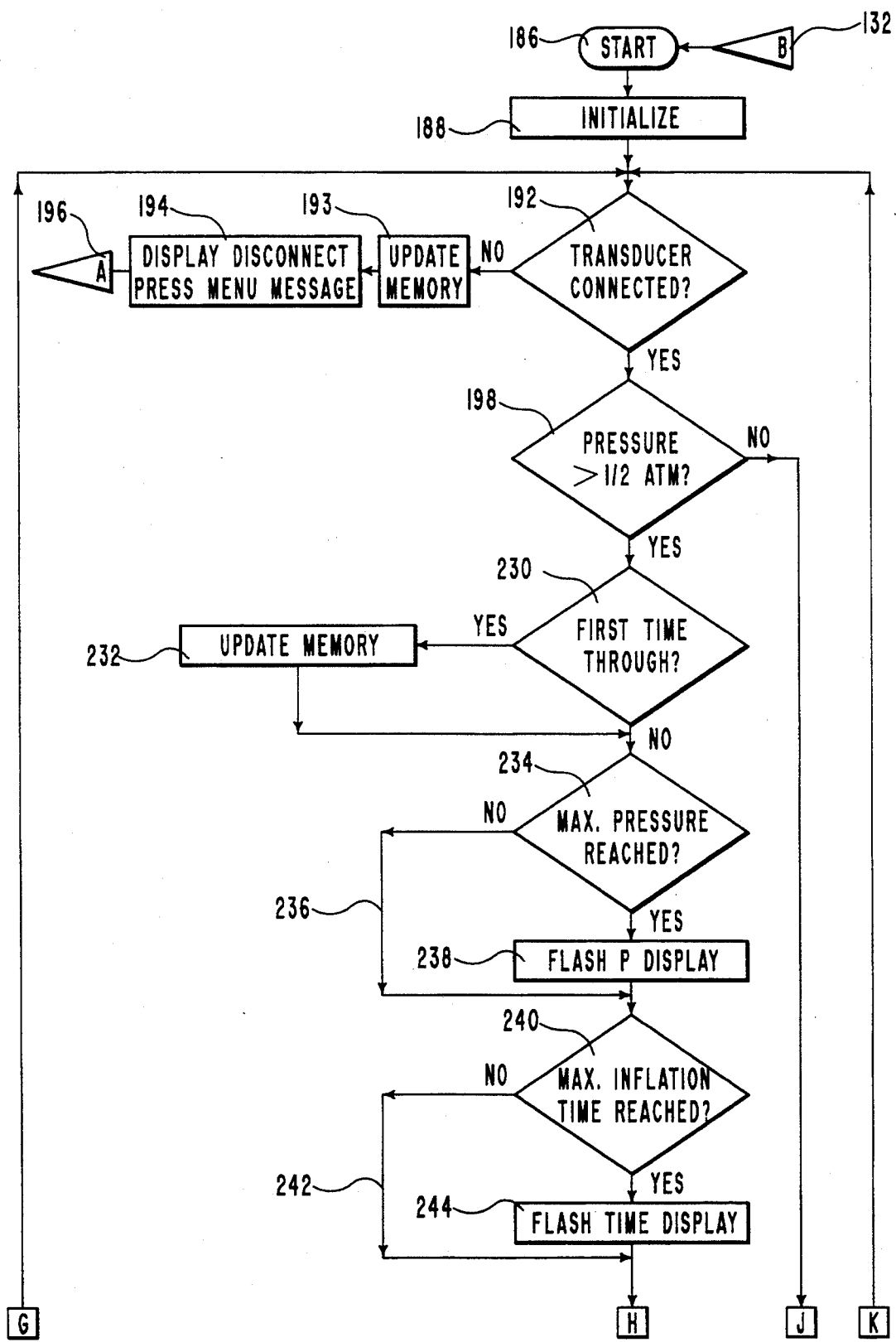

Once the transducer 42 has been connected to controller 20, the program moves through off page connector 132 in FIG. 6A to a corresponding connector 132 in FIG. 6D. Then the program starts at step 186 and then moves to step 188 where the electronic circuitry is permitted to stabilize in an initialization routine. At step 188 digital processor 90 delays all operation of the electronic circuitry for a selected period of time to permit the circuit components to reach a steady state so that transient conditions will not introduce any errors into the data. The program then moves to step 192.

At step 192 in FIG. 6D the program again undergoes a check to determine whether transducer 42 is still connected to controller 20. This is a safety precaution to make sure that at all times during the inflation and deflation procedure transducer 42 is electrically connected to controller 20 so that the balloon condition data is being accurately input, displayed and recorded. If transducer 42 is not connected, the program first updates data memory 96 (step 193) so as to mark the time of disconnection and then a message is output at digital readout 66 as indicated at step 194 of FIG. 6D which notifies the system user that transducer 42 is disconnected and instructs the system user to press menu switch 73. If transducer 42 is still connected, the program then moves to step 198 in FIG. 6D and begins to monitor the electrical signal from transducer 42, which signal has been digitized and input to digital processor 90 as previously described in connection with FIG. 4 and FIGS. 5A-D.

The signal from transducer 42 is monitored based on a sample rate that is a matter of design choice based upon the particular circuit design, which for the illustrated embodiment is ten times per second. If the sensed pressure at transducer 42 is detected at step 198 as less than one-half atmosphere (another threshold pressure level could also be pre-set here) indicating a balloon deflation condition, the program moves to that portion of the program which commences with step 200 in FIG. 6E.

At step 200 the program first determines whether it is in the first pass through the loop started by step 200, and if so, the program moves to step 202 where data memory 96 is updated.

Figure 6E:
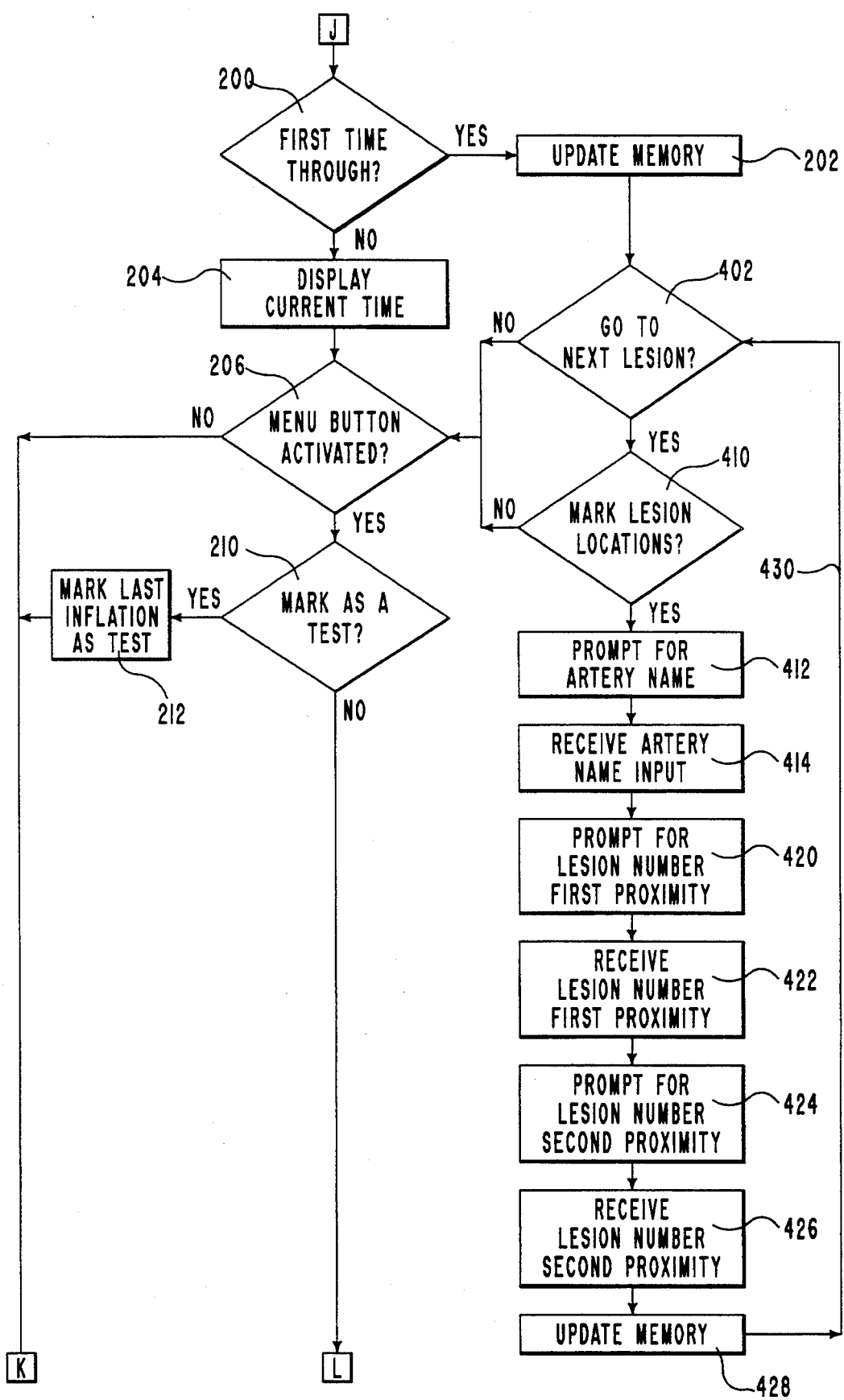
Figure 6F:
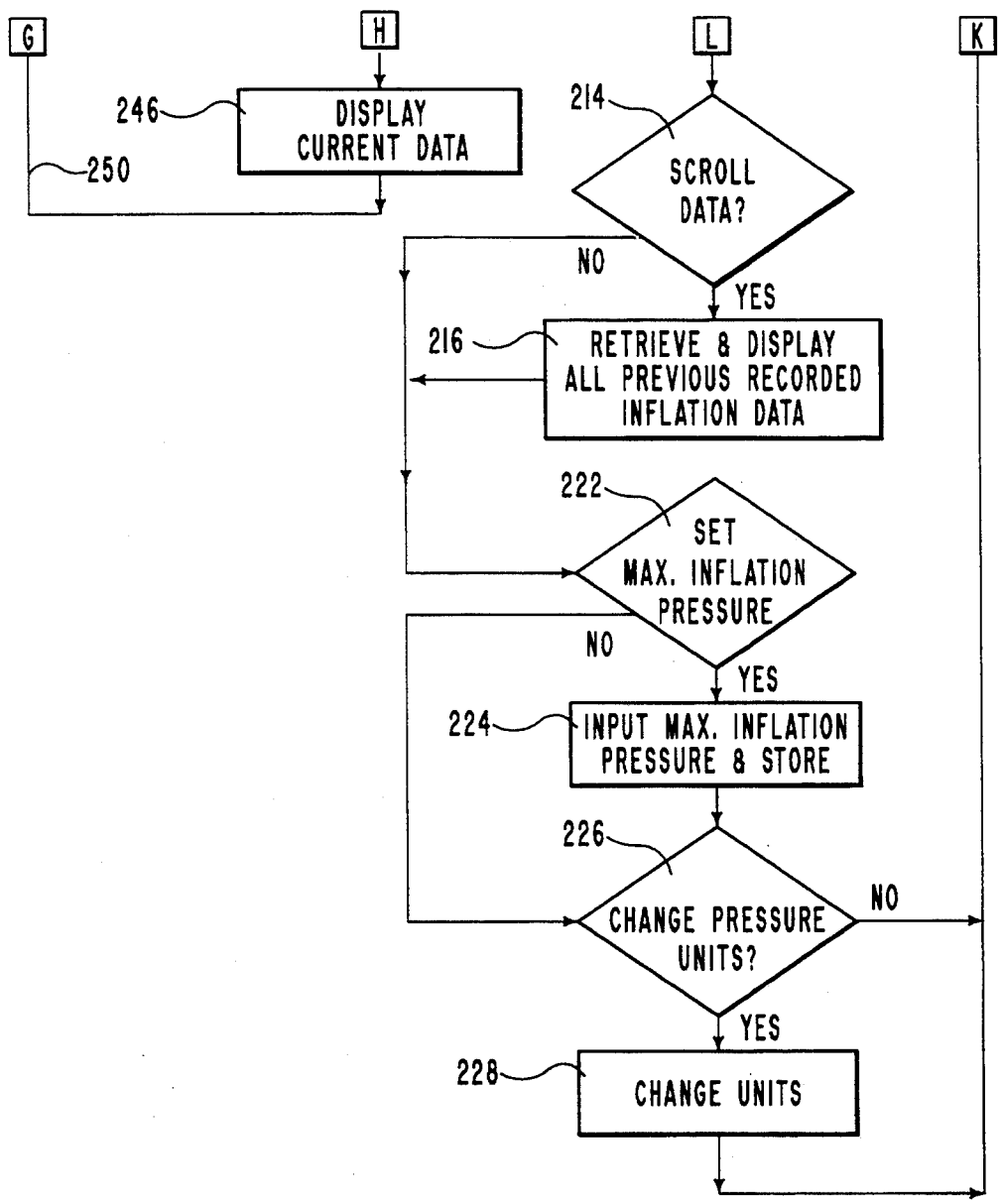

After the update to memory at step 202 in FIG. 6E, the system user is prompted at step 402 in FIG. 6E if the balloon catheter is to be relocated to the next lesion during the current deflation interval prior to the next inflation. If not, the program moves to step 206. If the operator answers affirmitivley that there will be a relocation of the balloon catheter, the program moves to step 410 in FIG. 6G for the purpose of allowing the system user to mark lesions to be operated upon.

After the system user affirmatively answers the prompt at step 410 in FIG. 6E, then the routine to mark lesions begins at step 412 in FIG. 6E at which the system user will be prompted for the name of the artery in which the lesion is located. This step causes a series of displays on digital readout 66 of control panel 64 displaying the name of an artery, in response to which the system user would input yes or no be pressing respectively menu or select switches 73, 75 to choose or to reject the particular displayed artery name.

After the system user has rejected artery names sequentially displayed upon digital readout 66 and has made a first selection of an artery name at step 414, steps 420 through 426 in FIG. 6E optionally accept system user input as to the relative location within the artery name selected by the input of two proximity identifiers. By way of example and not by way of limitation, the system user may be prompted for and may select or reject a proximity 1 or 2 level identifiers such as "proximal", "medial", or "distal." Again by way of example, the lesion identifying data selected by the system user for a particular lesion in step 412 through step 426 may be: "LAD" (left anterior descending artery); "medial" (first proximity indicator); and "2" (second proximity indicator).

At step 428 in FIG. 6E, data memory 96 is updated as to data input by the system user and the program moves back to step 402 in FIG. 6E where the system user can optionally choose to move the balloon catheter to the next lesion and to mark more lesions as previously described, or else the program will move to step 206 in FIG. 6E where the activation of menu switch 73 will be tested for, and if menu switch 73 is pressed the program will move to step 192 in FIG. 6D.

At step 402, if the system user responds to go to the next lesion, then the previously described sequence of steps 412 through 428 for the input of identifying data as to the next lesion will be executed. The next inflation interval, which will be first recognized by the program at step 198 in with step 200 in FIG. 6E, will record and display data at step 246 in FIG. 6F, including the lesion identification data input at steps 402 through 428. The program moves from step 402 or step 410, due to the system user's negative response, to step 206.

In an alternative to the above, if at step 200 the program determines that it is not making its first pass through the loop started by step 200, then the program moves directly to step 204 and displays the current data with respect to the deflation number, time, and the characters "NEG" indicating a deflation balloon condition. The effect of updating data memory 96 at step 202 is that the time with respect to termination of the last inflation (e.g. duration of the inflation interval) and the beginning of the deflation interval is recorded and stored in data memory 96.

After the current data is displayed at digital readout 66 of control panel 64 at step 204, the program then moves to step 206 where digital processor 90 checks for menu switch 73 activation. If menu switch 73 is activated at step 206 in FIG. 6E the program moves to the next step 210 in FIG. 6E where the last inflation data can be marked as an initial test as desired by the system user. This option of allows a system user to make a notation in data memory 96 indicating that derived data accumulated as to a particular inflation event is to be interpreted as only a test rather than as an actual applied inflation event. Such a data marking is requested by the system user using menu and select switches 73, 75 after a visual prompt to the system user at digital readout 66, such as "MARK AS TEST?".

If the initial inflation is merely a test, it is marked at step 212 prior to returning to step 192 in FIG. 6D. Otherwise, the program moves to step 214 in FIG. 6F to determine at step 214 whether any previously recorded inflation data is to be scrolled by visually displaying such data on digital readout 66. If the data is scrolled, the program moves to step 216 in FIG. 6F and retrieves and displays in sequence previously recorded balloon condition data for each prior balloon condition occurrence, after which the program jumps to step 222 in FIG. 6F.

The system user is prompted at step 222 to set a new maximum positive inflation pressure at step 224 and is prompted at step 226 to change the pressure measurement units at step 228 by entering any of these selections using select switch 75 after which the program jumps to step 192 in FIG. 6D. A negative response to any of the prompts in steps 214, 222, or 226 will cause the program to move to step 192 in FIG. 6D.

Once the inflation pressure applied to the balloon catheter begins to exceed one-half atmosphere by insertion of the syringe plunger, indicating a balloon inflation condition, the program moves from step 198 in FIG. 6D to step 230 in FIG. 6D. At step 230 the program determines whether this is the first time through the part of the program loop which beings with step 230 and if so updates data memory 96 at step 232.

The effect of updating the memory at step 232 is that digital processor 90 causes the time with respect to the termination of the last inflation (e.g. duration of the inflation interval) and the start of the next deflation interval to be recorded and stored in data memory 96. After the update of memory at step 232 has been performed, or in each subsequent pass through step 230, the program then moves to step 234 where the program checks to determine whether the inflation pressure has reached any selected maximum positive inflation pressure input for this inflation event. If the user selected maximum inflation pressure is reached the program moves to step 238 and causes pressure display 72 on control panel 64 to begin flashing so as to signal the system user that the selected maximum inflation pressure has been reached. If the selected maximum inflation pressure has not been reached or if none was selected, the program then jumps as illustrated at line 236 to step 240.

At step 240 in FIG. 6D the program checks to determine whether any selected duration has yet been clocked with respect to a selected duration for application of positive pressure and if so then moves to step 244 so as to cause time display portion 70 to begin flashing, thereby signalling the program user that the selected duration has been achieved. If no duration is input or if the selected duration has not been reached the program moves to step 246 in FIG. 6F as indicated at line 242 in FIG. 6D which causes the program to display the current data with respect to the inflation interval number, pressure being applied, and the length of time that positive inflation pressure has been applied. The program then returns to the beginning of the loop at step 192 in FIG. 6D to repeat the steps described above.

Another feature contemplated for use in the present invention, and previously mentioned herein, is the option of allowing a system user to cause the optionally connected peripheral printer (not shown) to print several manual entry note lines, thus leaving on the printout forms a note line upon which a note can be handwritten in the space provided by the note liner regarding the inflation performed by the system user. Such a request by the system user could be initiated from menu and select switches 73, 75 after a prompt to the system user upon digital readout 66 of console panel 66 with such an option. The request for a note line would be recorded in data memory 96 for later use by the system user as a written history of the medical procedure.

It will be appreciated that digital processor 90 of FIG. 5A, which is an 8032 microprocessor as identified in Table I, could be programmed so as to implement the above-described method using any one of a variety of different programming languages and programming techniques. Attached hereto as Exhibit A is one such program which was prepared for use with the 8032 microprocessor and the circuit configuration as illustrated in FIGS. 5A through 5D. The attached software program appendix in Exhibit A comprises a listing of source code language for the 8032 microprocessor.

The invention may be embodied in other specific forms without departing from its spirit or essential characteristics. Accordingly, the described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

TABLE I

| Schematic Reference | Part |
|---|---|
| X1 | 11.059 MHZ |
| C3 | 10 Mfd |
| R1 | 8.2K |
| U1 | 8032 |
| U2 | 74HC573 |
| C5, C7, C14 | .01 Mfd |
| C1, C2 | 33 pf |
| P1 | CONNECTOR DB25F AMP 745389-1 |
| U4 | DS1243 |
| U5, U6, U7 | DL3416 SIEMENS |
| U8 | ADC0834 TI |
| U9 | MAX233 |
| D1 | IN5291 |
| R4 | 30K |
| U3 | 27256 |
| U11 | UA7805UC FAIRCHILD |
| C4 | 4700 Mfd |
| PCB 1 | Printed circuit board |
| JP3 | Female RJ-11 (6 pos- 4 wire) |
| JP1 | HEADER 4 |
| J1 | AC line cord |
| R17 | MMSI TRANSDUCER |
| R3 | 33K |
| U10 | LM324 |
| R5 | 10K DIP |
| R7, R9, R10, R11 | 10K DIP |
| K6, R8 | 10K-15T VRN 752-208-103 |
| R12, R13 | 100K |
| R2 | 10K |
| C6, C8, C9, C10, C11, C12, C13 | .01 Mfd |
| C15, C16 | .2 Mfd |
| T1 | Toltek Custom transformer |

TABLE I-continued

| Schematic Reference | Part |
| --- | --- |
| D2 | GI 2KBP04 |
| F1 | .25 AMP |
| SW1 | Micro Switch & Cover |

What is claimed and desired to be secured by United States Patent is:

1. In a system comprising an inflatable balloon member connected through tubing to a syringe barrel and wherein a plunger slidably mounted within said barrel is moveable to selectively apply and then release fluid pressures exerted on said balloon member so as to selectively inflate said balloon member one or more times, a method of monitoring and recording data comprising the steps of:

electromagnetically coupling a transducer means for detecting pressure and for outputting a voltage in proportion thereto with a means for digital signal processing, said transducer means being in fluid communication with internal pressure of the syringe barrel;

connecting the balloon catheter member through the tubing to the syringe barrel;

electronically visually outputting a system user prompt requesting an inflation location identifier;

electronically accepting the inflation location identifier input from an input means operated by a system user;

inflating the balloon member by pushing the plunger into the syringe barrel so as to increase both the internal pressure of the syringe barrel and the pressure applied to the balloon member;

detecting an electromagnetic pressure signal output by the transducer means;

converting the pressure signal to a digital pressure signal using a means for A/D signal conversion;

automatically electronically digitally processing the digital pressure signal so as to automatically derive and automatically record with the inflation location identifier in the digital signal processor means electronic digital data representing the magnitude of the internal pressure in the syringe barrel and the length of time that fluid pressure is applied to the balloon member.

2. A method as recited in claim 1, further comprising the steps of:

electronically outputting a visual display of the magnitude, the corresponding length of time that fluid pressure is applied to the balloon member, and the inflation location identifier; and deflating the balloon member by pulling the plunger toward the rear of the syringe barrel so as to decrease the internal pressure in the syringe barrel.

3. The method recited in claim 2, further comprising the step of repeating said electronically visually outputting a system user prompt requesting an inflation location identifier step through said balloon deflation step in connection with a second inflation of the balloon member.

4. The method recited in claim 1, wherein prior to said step of electronically visually outputting a system user prompt requesting an inflation location identifier, a step is performed comprising the steps of:

electronically visually outputting a system user prompt requesting a series of predetermined inflation location identifiers;

electronically accepting the series of predetermined inflation location identifiers input from the input means operated by the system user;

automatically recording in the digital signal processor means the series of predetermined inflation location identifiers in said digital processor means;

wherein the step of electronically visually outputting a system user prompt requesting an inflation location identifier further comprises the step of electronically visually outputting each one of the predetermined inflation location identifiers in the series of predetermined inflation location identifiers recorded in said digital processor means; and wherein the step of electronically accepting the inflation location identifier input from an input means operated by a system user further comprises accepting input from the input means operated by a system user of one of the predetermined inflation location identifiers in the series of predetermined inflation location identifiers recorded in said digital processor means.

5. A method as recited in claim 4, further comprising the steps of:

electronically outputting a visual display of the magnitude, the corresponding length of time that fluid pressure is applied to the balloon member, and the inflation location identifier; and deflating the balloon member by pulling the plunger toward the rear of the syringe barrel so as to decrease the internal pressure in the syringe barrel.

6. The method recited in claim 5, further comprising the step of repeating said electronically visually outputting a system user prompt requesting an inflation location identifier step through said balloon deflation step for each one of the predetermined inflation location identifiers in the series of predetermined inflation location identifiers recorded in said digital processor means.

7. The method recited in claim 4, wherein each one of the predetermined inflation location identifiers in the series of predetermined inflation location identifiers recorded in said digital processor means comprises an artery name, a lesion number first proximity, and a lesion number second proximity.

8. The method recited in claim 1, wherein the inflation location identifier comprises an artery name, a lesion number first proximity, and a lesion number second proximity.

9. The method recited in claim 1, wherein said step of electronically visually outputting a system user prompt requesting an inflation location identifier comprises electronically visually outputting a system user prompt requesting an artery name, a lesion number first proximity, and a lesion number second proximity.

10. A system for monitoring inflation and deflation of a balloon-type member and for automatically displaying or recording inflation and deflation data, comprising:

a syringe for connection to said balloon-type member through tubing, said syringe comprising a barrel and a plunger selectively operable to inflate said balloon-type member by applying fluid pressure to said balloon-type member through said tubing by sliding the plunger within the barrel, and to deflate said balloon-type member by withdrawing the plunger so as to release the fluid pressure;

transducer means for sensing the presence or absence of applied fluid pressure and for outputting an electrical signal proportional to said sensed presence or absence of fluid pressure, said transducer means being placed in fluid communication with said syringe and the tubing connected thereto;

input means, manually operable by a system user, for inputting an inflation location identifier;

electronic circuit means, electronically connected to the transducer means and the input means, for receiving said electrical signal and for electronically processing said signal, whereby said electronic circuit means derives and automatically displays or records therefrom electronic data representing the inflation location identifier, the magnitude of said fluid pressure when applied to said balloon-type member, and the length of time said fluid pressure is applied to said balloon-type member and the absence of fluid pressure and the length of time said fluid pressure is absent and the balloon-type member is deflated; and display means, electronically connected to said electronic circuit means, for outputting a visual display of the inflation location identifier, the magnitude of said fluid pressure when applied, and the corresponding length of time said pressure is applied to said balloon-type member, said display means including a digital readout.

11. The system as defined in claim 10, wherein the input means comprises:

first switch means for selecting a menu display stored in said electronic circuit means for presentation at said digital readout optionally selectable components of the inflation location identifier; and second switch means for entering to said electronic circuit means data identifying choices selected with respect to said optionally selectable components of the inflation location identifier.

12. The system as defined in claim 11, wherein said components of the inflation location identifier comprises:

an artery name, a lesion number first proximity, and a lesion number second proximity.

13. A system for generating a series of discrete balloon catheter inflation and deflation balloon conditions and for displaying data corresponding to each said discrete balloon condition comprising:

a control syringe for connection to a balloon of said balloon catheter through tubing, said syringe comprising a barrel and a plunger selectively operable to apply or remove fluid pressures from said balloon through said tubing by sliding the plunger respectively into and then withdrawing the plunger out of the barrel;

a piezoresistive semiconductor transducer connected in fluid communication with said fluid pressures applied to said balloon such that said transducer senses the presence or absence of fluid pressures applied to said balloon and generates an electrical signal proportional to the sensed pressure or absence of fluid pressure;

input means, manually operable by a system user, for inputting an inflation location identifier;

a display means for outputting a visual display; and a controller for housing said display means and electrically connected to said transducer and said input means, said controller comprising:

means for amplifying said signal output by said transducer;

means for converting said amplified signal from an analog to a digital signal form;

digital processor means for processing said digital signal form;

data memory means for storing digital data;

program memory means for storing machine-readable instructions utilized by said digital processor means; and a control panel;

said display means comprising a digital readout on said control panel; and said digital processor means responding to said machine-readable instructions to electronically derive, store in said data memory means, and digitally display both a first condition of inflation and the duration thereof with the inflation location identifier and a second condition of essentially total deflation and the duration thereof.

14. The system as defined in claim 13, wherein the input means comprises:

first switch means for selecting a menu display stored in said program memory means for presentation at said digital readout optionally selectable components of the inflation location identifier; and second switch means for entering to said electronic circuit means data identifying choices selected with respect to said optionally selectable components of the inflation location identifier.

15. The system as defined in claim 14, wherein said components of the inflation location identifier comprises:

an artery name, a lesion number first proximity, and a lesion number second proximity.

16. A system for monitoring a balloon-type member that is selectively inflated and deflated and for displaying the condition of the balloon-type member, comprising:

a syringe for connection to said balloon-type member through tubing, said syringe comprising a barrel and a plunger selectively operable to inflate said balloon-type member by sliding the plunger into the barrel to apply fluid pressure, and by withdrawing the plunger from the barrel to essentially totally deflate the balloon-type member;

transducer means for sensing whether the balloon-type member is inflated due to applied fluid pressure or is deflated due to removal of applied fluid pressure and for outputting an electrical signal proportional to said sensed fluid pressure, said transducer means being placed in fluid communication with said syringe and the tubing connected thereto;

input means, manually operable by a system user, for inputting an inflation location identifier;

electronic circuit means, operatively connected to said transducer means, said input means, and said display means, for processing said electrical signal, wherein said electronic circuit means comprises:

means for converting said signal output from said transducer means into a series of corresponding digital signals;

data memory means for storing digital data for later retrieval and output;

digital display means for outputting a visual digital display;

program memory means for storing machine readable instructions to carry out programmed steps; and digital processor means, operatively connected to said data memory means, said program memory means and said display means, for processing said digital signals in accordance with the programmed steps so as to electronically monitor, store in said data memory means and display at said digital display means the inflation location identifier with both a status of pressure applied to said balloon-type member during a first condition of inflation and the corresponding duration thereof and a status of the removal of applied pressure during a second condition of essentially total deflation of the balloon-type member and the corresponding duration thereof, said digital processor means performing the steps of:

calculating from said digital signals a numerical value of the magnitude of said applied pressure;

deriving data representing said status of pressure being applied to said balloon-type member from a comparison of said numerical value of the magnitude of said applied pressure to a pre-set numerical value;

electronically storing in the data memory means the inflation location identifier with all said derived data for retrieval and output; and automatically displaying the inflation location identifier with said derived data in a visually perceptible manner.

17. The system as defined in claim 16, wherein the input means comprises:

first switch means for selecting a menu display stored in said program memory means for presentation at said digital readout optionally selectable components of the inflation location identifier; and second switch means for entering to said electronic circuit means data identifying choices selected with respect to said optionally selectable components of the inflation location identifier.

18. The system as defined in claim 17, wherein said components of the inflation location identifier comprises:

an artery name, a lesion number first proximity, and a lesion number second proximity.

19. A system for generating a series of discrete balloon catheter inflation and deflation balloon conditions and for displaying data corresponding to each said discrete balloon condition comprising:

a control syringe for connection to a balloon of said balloon catheter through tubing, said syringe comprising a barrel and a plunger selectively operable to apply or remove fluid pressures from said balloon through said tubing by sliding the plunger respectively into and then withdrawing the plunger out of the barrel;

a piezoresistive semiconductor transducer connected in fluid communication with said fluid pressures applied to said balloon such that said transducer senses the presence or absence of fluid pressures applied to said balloon and generates an electrical signal proportional to the sensed pressure or absence of fluid pressure;

a display means comprising a digital readout for outputting a visual display;

a controller electrically connected to said transducer, said controller comprising:

means for amplifying said signal output by said transducer;

means for converting said amplified signal from an analog to a digital signal form;

digital processor means for processing said digital signal form;

data memory means for storing digital data; and program memory means for storing machine-readable instructions utilized by said digital processor means; and an input means comprising:

first switch means for selecting a menu display stored in said program memory means for presentation at said digital readout optionally selectable components of an inflation location identifier; and second switch means for entering to said data memory means data identifying choices selected with respect to said optionally selectable components of the inflation location identifier;

said digital processor means responding to said machine-readable instructions to electronically derive, store in said data memory means, and digitally display both a first condition of inflation and the duration thereof with the data identifying choices selected with respect to said optionally selectable components of the inflation location identifier and a second condition of essentially total deflation and the duration thereof.

20. The system as defined in claim 19, wherein said components of the inflation location identifier comprises:

an artery name, a lesion number first proximity, and a lesion number second proximity.

* * * * *

UNITED STATES PATENT AND TRADEMARK OFFICE
CERTIFICATE OF CORRECTION

PATENT NO. : 5,425,713
DATED : June 20, 1995
INVENTOR(S) : STEVEN R. TAYLOR et al.

It is certified that error appears in the above-indentified patent and that said Letters Patent is hereby corrected as shown below:

```
Column 1, line 16, delete "2"
Column 4, line 68, "preferrably" should be --preferably--
Column 9, line 10, delete "has"
Column 11, line 47, "during of a" should be --during a--
Column 12, line 33, "circuit US." should be --circuit U8.--
Column 14, line 7, "over writing" should be --overwriting--
Column 14, line 14, "over written" should be --overwritten--
Column 19, line 1, delete "of"
Column 19, line 34, "beings" should be --begins--
Column 25, lines 39-40, "comprises" should be --comprise--
```

Signed and Sealed this

Twenty-sixth Day of December, 1995

*Attest:*

BRUCE LEHMAN

*Attesting Officer*   Commissioner of Patents and Trademarks